United States Patent
Tsai et al.

(10) Patent No.: US 10,526,589 B2
(45) Date of Patent: Jan. 7, 2020

(54) MULTIPLEX GUIDE RNAS

(71) Applicant: The General Hospital Corporation, Boston, MA (US)

(72) Inventors: Shengdar Tsai, Charlestown, MA (US); J. Keith Joung, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/107,550

(22) PCT Filed: Sep. 18, 2014

(86) PCT No.: PCT/US2014/056416
§ 371 (c)(1),
(2) Date: Jun. 23, 2016

(87) PCT Pub. No.: WO2015/099850
PCT Pub. Date: Jul. 2, 2015

(65) Prior Publication Data
US 2016/0319281 A1 Nov. 3, 2016

Related U.S. Application Data

(63) Continuation of application No. 14/211,117, filed on Mar. 14, 2014, and a continuation of application No. PCT/US2014/029068, filed on Mar. 14, 2014, and a continuation of application No. PCT/US2014/029304, filed on Mar. 14, 2014, and a continuation of application No. PCT/US2014/028630, filed on Mar. 14, 2014, and a continuation of application No. PCT/US2014/035162, filed on Apr. 23, 2014.

(60) Provisional application No. 61/921,007, filed on Dec. 26, 2013, provisional application No. 61/930,782, filed on Jan. 23, 2014.

(51) Int. Cl.
*C12N 9/22* (2006.01)
*C12P 19/34* (2006.01)
*C07K 14/47* (2006.01)
*C12N 15/63* (2006.01)
*C12N 15/113* (2010.01)

(52) U.S. Cl.
CPC ............ *C12N 9/22* (2013.01); *C07K 14/4705* (2013.01); *C12N 15/1136* (2013.01); *C12N 15/63* (2013.01); *C07K 2319/40* (2013.01); *C07K 2319/43* (2013.01); *C07K 2319/80* (2013.01); *C12N 2310/20* (2017.05); *C12N 2310/318* (2013.01); *C12N 2310/3231* (2013.01); *C12N 2310/3341* (2013.01)

(58) Field of Classification Search
None
See application file for complete search history.

(56) References Cited

U.S. PATENT DOCUMENTS

| | | |
|---|---|---|
| 4,603,044 A | 7/1986 | Geho et al. |
| 4,957,773 A | 9/1990 | Spencer et al. |
| 5,436,150 A | 7/1995 | Srinivasan |
| 6,007,988 A | 12/1999 | Choo et al. |
| 6,013,453 A | 1/2000 | Choo et al. |
| 6,503,717 B2 | 1/2003 | Case et al. |
| 6,511,808 B2 | 1/2003 | Wolffe et al. |
| 7,021,555 B2 | 4/2006 | Bagnall |
| 7,220,719 B2 | 5/2007 | Case |
| 7,914,796 B2 | 3/2011 | Miller |
| 7,919,277 B2 | 4/2011 | Russell et al. |
| 8,034,598 B2 | 10/2011 | Miller |
| 8,071,370 B2 | 12/2011 | Wolffe |
| 8,252,535 B2 | 8/2012 | Biekle et al. |
| 8,282,920 B2 | 10/2012 | Heo et al. |
| 8,361,725 B2 | 1/2013 | Russell et al. |
| 8,697,359 B1 | 4/2014 | Zhang |
| 8,771,986 B2 | 7/2014 | Miller |
| 8,865,406 B2 | 10/2014 | Zhang et al. |
| 8,962,281 B2 | 2/2015 | Doyon |
| 8,993,233 B2 | 3/2015 | Zhang et al. |
| 9,023,649 B2 | 5/2015 | Mali et al. |
| 9,074,199 B1 | 7/2015 | Chavez et al. |
| 9,322,037 B2 | 4/2016 | Liu et al. |
| 9,926,546 B2 | 3/2017 | Joung et al. |
| 9,771,601 B2 | 9/2017 | May et al. |

(Continued)

FOREIGN PATENT DOCUMENTS

| CN | 103224947 | 7/2013 |
|---|---|---|
| CN | 103233028 | 8/2013 |

(Continued)

OTHER PUBLICATIONS

Sequence Alignment instant SEQ ID No. 1 with SEQ ID No. 103. Search conducted on Feb. 15, 2018, 1 page.*
European Office Action in Application No. 14764159.1, dated Jun. 16, 2017, 4 pages.
European Office Action in Application No. 14764117.9, dated Jul. 6, 2017, 4 pages.
European Office Action in Application No. 14768877.4, dated Jul. 14, 2017, 4 pages.

(Continued)

*Primary Examiner* — Channing S Mahatan
(74) *Attorney, Agent, or Firm* — Fish & Richardson P.C.

(57) ABSTRACT

Methods and constructs for the multiplex expression of highly active CRISPR guide RNAs (gRNAs) from RNA Polymerase II and III promoters, optionally in mammalian cells. The present invention is based, at least in part, on the discovery that Csy4, an endoribonuclease that recognizes a short RNA hairpin sequence, can be used to cleave out multiple functional gRNAs encoded on a single longer RNA transcript (produced from an RNA pol II or III promoter) in which the individual gRNAs are separated by Csy4 cleavage sites.

20 Claims, 9 Drawing Sheets

Specification includes a Sequence Listing.

(56) References Cited

U.S. PATENT DOCUMENTS

| | | |
|---|---|---|
| 9,885,033 B2 * | 2/2018 | Joung ................. C12N 15/102 |
| 2002/0160940 A1 | 10/2002 | Case et al. |
| 2002/0164575 A1 | 11/2002 | Case et al. |
| 2005/0214851 A1 | 9/2005 | Arts et al. |
| 2006/0199190 A1 | 9/2006 | Russell et al. |
| 2007/0020627 A1 | 1/2007 | Barbas, III |
| 2008/0124725 A1 | 5/2008 | Barrangou et al. |
| 2008/0193470 A1 | 8/2008 | Masignani et al. |
| 2010/0034924 A1 | 2/2010 | Fremaux et al. |
| 2010/0055793 A1 | 3/2010 | Chandrasegaran |
| 2010/0076057 A1 | 3/2010 | Sontheimer et al. |
| 2010/0093617 A1 | 4/2010 | Barrangou et al. |
| 2010/0104690 A1 | 4/2010 | Barrangou et al. |
| 2010/0120043 A1 | 5/2010 | Sood et al. |
| 2010/0183559 A1 | 7/2010 | Van Sinderen et al. |
| 2010/0184624 A1 | 7/2010 | Samuel et al. |
| 2010/0209998 A1 | 8/2010 | Attwood et al. |
| 2010/0209999 A1 | 8/2010 | Altermann et al. |
| 2010/0221185 A1 | 9/2010 | Altermann et al. |
| 2010/0311061 A1 | 12/2010 | Korlach et al. |
| 2010/0317116 A1 | 12/2010 | Flusberg et al. |
| 2011/0002889 A1 | 1/2011 | Barrangou et al. |
| 2011/0092381 A1 | 4/2011 | Sood et al. |
| 2011/0143348 A1 | 6/2011 | Tomigahara et al. |
| 2011/0150852 A1 | 6/2011 | Chambaud et al. |
| 2011/0171647 A1 | 7/2011 | Tomigahara et al. |
| 2011/0189674 A1 | 8/2011 | Tomigahara et al. |
| 2011/0189776 A1 | 8/2011 | Terns et al. |
| 2011/0201007 A1 | 8/2011 | Waller et al. |
| 2011/0201118 A1 | 8/2011 | Yang et al. |
| 2011/0217739 A1 | 9/2011 | Terns et al. |
| 2011/0217791 A1 | 9/2011 | Tomigahara et al. |
| 2011/0223638 A1 | 9/2011 | Wiedenheft et al. |
| 2011/0236530 A1 | 9/2011 | Manoury et al. |
| 2011/0236894 A1 | 9/2011 | Rao et al. |
| 2011/0269119 A1 | 11/2011 | Hutchison et al. |
| 2011/0300528 A1 | 12/2011 | Jassim et al. |
| 2011/0300538 A1 | 12/2011 | Barrangou et al. |
| 2012/0027786 A1 | 2/2012 | Gupta et al. |
| 2012/0088676 A1 | 4/2012 | Weill et al. |
| 2012/0151635 A1 | 6/2012 | Coruzzi et al. |
| 2012/0214160 A1 | 8/2012 | Deng et al. |
| 2013/0011516 A1 | 1/2013 | Griffin et al. |
| 2013/0011828 A1 | 1/2013 | Barrangou et al. |
| 2013/0130248 A1 | 5/2013 | Haurwitz et al. |
| 2013/0145497 A1 | 6/2013 | Choi et al. |
| 2013/0150240 A1 | 6/2013 | Newman et al. |
| 2013/0158245 A1 | 6/2013 | Russell et al. |
| 2013/0253040 A1 | 9/2013 | Miller et al. |
| 2013/0288251 A1 | 10/2013 | Horvath et al. |
| 2013/0326645 A1 | 12/2013 | Cost et al. |
| 2013/0326725 A1 | 12/2013 | Shukla et al. |
| 2013/0330778 A1 | 12/2013 | Zeiner et al. |
| 2013/0337454 A1 | 12/2013 | Duchateau |
| 2014/0068797 A1 | 3/2014 | Doudna et al. |
| 2014/0093941 A1 | 4/2014 | Terns et al. |
| 2014/0113376 A1 | 4/2014 | Sorek et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273037 A1 | 9/2014 | Wu |
| 2014/0273226 A1 | 9/2014 | Wu |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas et al. |
| 2014/0287938 A1 | 9/2014 | Zhang et al. |
| 2014/0294773 A1 | 10/2014 | Brouns et al. |
| 2014/0295556 A1 | 10/2014 | Joung et al. |
| 2014/0295557 A1 | 10/2014 | Joung et al. |
| 2014/0298547 A1 | 10/2014 | Sasty-Dent et al. |
| 2014/0304853 A1 | 10/2014 | Ainley et al. |
| 2014/0309487 A1 | 10/2014 | Lee et al. |
| 2014/0310828 A1 | 10/2014 | Lee et al. |
| 2014/0310830 A1 | 10/2014 | Zhang et al. |
| 2014/0315985 A1 | 10/2014 | May et al. |
| 2014/0335063 A1 | 11/2014 | Cannon et al. |
| 2014/0335620 A1 | 11/2014 | Zhang et al. |
| 2014/0349400 A1 | 11/2014 | Jakimo et al. |
| 2014/0356867 A1 | 12/2014 | Peter et al. |
| 2014/0356958 A1 | 12/2014 | Mali et al. |
| 2014/0357530 A1 | 12/2014 | Zhang et al. |
| 2014/0377868 A1 | 12/2014 | Joung et al. |
| 2015/0020223 A1 | 1/2015 | Zhang et al. |
| 2015/0024499 A1 | 1/2015 | Brouns et al. |
| 2015/0024500 A1 | 1/2015 | Yu et al. |
| 2015/0031134 A1 | 1/2015 | Zhang et al. |
| 2015/0044772 A1 | 2/2015 | Zhao |
| 2015/0045546 A1 | 2/2015 | Siksnys et al. |
| 2015/0050699 A1 | 2/2015 | Siksnys et al. |
| 2015/0056629 A1 | 2/2015 | Guthrie-Honea |
| 2015/0067922 A1 | 3/2015 | Yang et al. |
| 2015/0071899 A1 | 3/2015 | Liu et al. |
| 2015/0079681 A1 | 3/2015 | Zhang |
| 2015/0093473 A1 | 4/2015 | Barrangou et al. |
| 2015/0159174 A1 | 6/2015 | Frendeway et al. |
| 2015/0159175 A1 | 6/2015 | Frendeway et al. |
| 2015/0166969 A1 | 6/2015 | Takeuchi et al. |
| 2015/0167000 A1 | 6/2015 | Voytas et al. |
| 2015/0176064 A1 | 6/2015 | Fach et al. |
| 2015/0184139 A1 | 7/2015 | Zhang et al. |
| 2015/0191744 A1 | 7/2015 | Wolfe et al. |
| 2015/0203872 A1 | 7/2015 | Zhang |
| 2015/0232882 A1 | 8/2015 | Zhang et al. |
| 2015/0232883 A1 | 8/2015 | Dahlman et al. |
| 2015/0247150 A1 | 9/2015 | Zhang et al. |
| 2015/0252358 A1 | 9/2015 | Maeder et al. |
| 2015/0291965 A1 | 10/2015 | Zhang et al. |
| 2015/0291966 A1 | 10/2015 | Zhang et al. |
| 2015/0315576 A1 | 11/2015 | Caliando et al. |
| 2015/0356239 A1 | 12/2015 | Zhang et al. |
| 2015/0376652 A1 | 12/2015 | Kuhn et al. |
| 2016/0010076 A1 | 1/2016 | Joung et al. |
| 2016/0010147 A1 | 1/2016 | Heron |
| 2016/0017301 A1 | 1/2016 | Khalili et al. |
| 2016/0017366 A1 | 1/2016 | Chen et al. |
| 2016/0024510 A1 | 1/2016 | Bikard et al. |
| 2016/0024523 A1 | 1/2016 | Joung et al. |
| 2016/0024524 A1 | 1/2016 | Joung et al. |
| 2016/0024529 A1 | 1/2016 | Carstens et al. |
| 2016/0312198 A1 | 10/2016 | Joung et al. |
| 2016/0362688 A1 | 12/2016 | May et al. |

FOREIGN PATENT DOCUMENTS

| | | |
|---|---|---|
| CN | 103343120 | 10/2013 |
| EP | 2325332 | 5/2011 |
| WO | WO 2003/072788 | 9/2003 |
| WO | WO 2004/099366 | 11/2004 |
| WO | WO 2007/014275 | 2/2007 |
| WO | WO 2007/025097 | 3/2007 |
| WO | WO 2008/108989 | 9/2008 |
| WO | WO 2010/054108 | 5/2010 |
| WO | WO 2011/017293 | 2/2011 |
| WO | WO 2011/143124 | 11/2011 |
| WO | WO 2012/093833 | 7/2012 |
| WO | WO 2012/164565 | 12/2012 |

(56) References Cited

FOREIGN PATENT DOCUMENTS

| WO | WO 2013/012674 | 1/2013 |
|---|---|---|
| WO | WO 2013/098244 | 7/2013 |
| WO | WO 2013/141680 | 9/2013 |
| WO | WO 2013/142578 | 9/2013 |
| WO | WO 2013/169398 | 11/2013 |
| WO | WO 2013/176772 | 11/2013 |
| WO | WO 2014/059255 | 4/2014 |
| WO | WO 2014/089290 | 6/2014 |
| WO | WO 2014/093655 | 6/2014 |
| WO | WO 2014/099744 | 6/2014 |
| WO | WO 2014/124284 | 8/2014 |
| WO | WO 2014/127287 | 8/2014 |
| WO | WO 2014/144288 | 9/2014 |
| WO | WO 2014/144761 | 9/2014 |
| WO | WO 2014/152432 | 9/2014 |
| WO | WO 2014/204578 | 12/2014 |
| WO | WO 2015/035162 | 3/2015 |
| WO | WO 2015/089364 | 6/2015 |
| WO | WO 2015/099850 | 7/2015 |
| WO | WO 2015/153940 | 10/2015 |
| WO | WO 2016/115355 | 6/2016 |
| WO | WO 2014/144592 | 9/2017 |

OTHER PUBLICATIONS

Office Action in U.S. Appl. No. 14/775,930, dated Sep. 21, 2017, 23 pages.
Office Action in Canadian Application No. 2907198, dated Aug. 24, 2017, 10 pages.
Office Action in U.S. Appl. No. 14/776,620, dated Sep. 28, 2017, 8 pages.
Addgene.org [Online]. CRISPR/Cas9 Guide on the web, Jan. 2016, [retrieved on Sep. 13, 2016]. Retrieved from the internet: URL<http://www.addgene.org/CRISPR/guide>/. 146 pages.
Gaj et al., ZFN, TALEN, and CRISPR/Cas-based methods for genome engineering, Trends in Biotechnology, Jul. 2013, 31(7): 397-405.
International Search Report and Written Opinion in International Application No. PCT/US2013/074736, dated Sep. 17, 2014, 4 pages.
International Search Report and Written Opinion in International Application No. PCT/US16/49147, dated Dec. 23, 2016, 12 pages.
International Search Report in International Application No. PCT/US2014/054291, dated Mar. 27, 2015, 6 pages.
Invitation to Pay Additional Fees and, Where Applicable, Protest Fee in International application No. PCT/US2016/49147, dated Oct. 31, 2016, 2 pages.
Jinek et al., "Supplementary Materials for a Programmable Dual-RNA-Guided DNA Endonuclease in Adaptive Bacterial Immunity," Science, Aug. 2012, pp. 1-37.
Kleinstiver et al., "High-fidelity CR1SPR-Cas9 nucleases with no detectable genome-wide off target effects," Nature, Jan. 2016, 529: 490-495.
Office Action in Australian Application No. 2014227653, dated Nov. 18, 2016, 3 pages.
Office Action in U.S. Appl. No. 14/775,930, dated Feb. 27, 2017, 55 pages.
Slaymaker et al. "Rationally engineered Cas9 nucleases with improved specificity", Science, Jan. 2016,351(6268): 84-88.
Chinese Office Action in Application No. 201480026113.4, dated May 31, 2017, 21 pages (with English translation).
Extended European Search Report in Application No. 14875819.6, dated Jun. 8, 2017, 11 pages.
Office Action in European Application No. 14763916.5, dated Mar. 27, 2017, 6 pages.
Office Action in U.S. Appl. No. 14/776,620, dated Mar. 31, 2017, 45 pages.
U.S. Appl. No. 61/610,212, filed Mar. 13, 2012, Joung et al.
U.S. Appl. No. 61/799,647, filed Mar. 15, 2013, Joung et al.
U.S. Appl. No. 61/838,148, filed Jun. 21, 2013, Joung et al.
U.S. Appl. No. 61/838,178, filed Jun. 21, 2013, Joung et al.

Al-Attar et al., "Clustered regularly interspaced short palindromic repeats (CRISPRs): the hallmark of an ingenious antiviral defense mechanism in prokaryotes," Biol Chem., Apr. 2011, 392:277-289.
Alexopoulou et al., "The CMV early enhancer/chicken β actin (CAG) promoter can be used to drive transgene expression during the differentiation of murine embryonic stem cells into vascular progenitors," BMC Cell Biology, 2008, 9:2.
Anders et al., "Structural basis of PAM-dependent target DNA recognition by the Cas9 endonuclease," Nature, 2014, 513:569-573.
Anonymous, "2013 Runners-Up. Genetic microsurgery for the masses," Science. Dec. 20, 2013;342(6165): 1434-5.
Appela., "Non-natural nucleic acids for synthetic biology", Current Opinion in Chemical Biology, Dec. 2009,13(5-6): 687-696.
Arimondo et al., "Exploring the Cellular Activity of Camptothecin—Triple-Helix-Forming Oligonucleotide Conjugates," Mol. Cell. Biol., 26(1):324-33 (2006).
Amould et al., "Engineering of large numbers of highly specific homing endonucleases that induce recombination on novel DNA targets," J Mol Biol., 355(3):443-458, Epub Nov. 15, 2005.
Arnould et al., "The I-CreI meganuclease and its engineered derivatives: applications from cell modification to gene therapy," Protein Eng Des Sel., 24(1-2):27-31, Epub Nov. 3, 2010.
Arora et at, "Residues 1-254 of anthrax toxin lethal factor are sufficient to cause cellular uptake of fused polypeptides," J. Biol. Chem., Feb. 1993, 268:3334-41.
Auer et al., "Highly efficient CRISPR/Case9-mediated known-in in zebrafish by homology-independent DNA repair," Genome Res., 2014, 24:142-153.
Bae et al., "Cas-OFFinder: a fast and versatile algorithm that searches for potential off-target sites of Cas9 RNA-guided endonucleases," Bioinformatics, 2014, 30:1473-1475.
Bae et al., "Human zinc fingers as building blocks in the construction of artificial transcription factors," Nat Biotechnol., 21(3):275-280, Epub Feb. 18, 2003.
Barker et at, "Increased DNA microarray hybridization specificity using sscDNA targets," BMC Genomics, Apr. 2005, 6:57, 8 pages.
Baron-Benhamou et al., "Using the λN Peptide to Tether Proteins to RNAs," Methods Mole Biol., Jan. 2004, 257:135-153.
Barrangou & May, "Unraveling the potential of CRISPR-Cas9 for gene therapy," Expert Opin. Biol. Ther., 2015, 15:311-314.
Barrangou et al., "CRISPR Provides Acquired Resistance Against Viruses in Prokaryotes," Sci., 2007, 315:1709-1712.
Barrangou, "RNA-mediated programmable DNA cleavage," Nature Biotechnol., 2012, 30(9).836-838.
Bassett et al., "Highly efficient targeted mutagenesis of *Drosophila* with the CRISPR/Cas9 system," Cell Reports, 2013, 4:220-228.
Beerli and Barbas, "Engineering polydactyl zinc-finger transcription factors," Nat Biotechnol., 20(2):135-141, Feb. 2002.
Beerli et al., "Toward controlling gene expression at will: specific regulation of the erbB-2/HER-2 promoter by using polydactyl zinc finger proteins constructed from modular building blocks," PNAS USA, 1998, 95:14628-14633.
Belhaj et al., "Plant genome editing made easy: targeted mutagenesis in model and crop plants using the CRISPR/Cas system," Plant Methods, 2013, 9:39, 10 pages.
Bello et al., "Hypermethylation of the DNA repair gene MGMT: association with TP53 G:C to A:T transitions in a series of 469 nervous system tumors," Mutat. Res., Oct. 2004, 554:23-32.
Berg, "Proposed structure for the zinc-binding domains from transcription factor IIIA and related proteins," Proc Natl Acad Sci U S A., 85(1):99-102, Jan. 1988.
Bikard et al., "Programmable repression and activation of bacterial gene expression using an engineered CRISPR-Cas system," Nucleic Acid Res., Jun. 2013 41(15):7429-7437.
Bitinaite et al., "Fold dimerization is required for DNA cleavage," Proc. Natl. Acad. Sci. USA, 1998, 95:10570-10575.
Blackburn et al., "The CRISPR System-Keeping Zebrafish Gene Targeting Fresh," Zebrafish, 2013, 10(1):116-118.
Blaese et al., "T lymphocyte-directed gene therapy for ADA-SCID: initial trial results after 4 years," Science, Oct. 1995, 270:475-480.
Boch et al., "Breaking the code of DNA binding specificity of TAL-type II effectors," Science, Dec. 11, 2009;326(5959):1509-12.

(56) References Cited

OTHER PUBLICATIONS

Bogdanove & Voytas, "TAL Effectors: Customizable Proteins for DNA Targeting," Science, 333:1843-1846 (2011).
Bogdanove et al., "TAL effectors: finding plant genes for disease and defense," Curr. Opin. Plant Biol., 13:394-401 (2010).
Burgess, "A CRISPR genome-editing tool," Nature Reviews Genetics 14, 80-81 (Feb. 2013).
Burnett et al., "Conditional macrophage ablation in transgenic mice expressing a Fas-based suicide gene," J. Leukoc. Biol., Apr. 2004, 75(4):612-623.
Butler and Kadonaga, "The RNA polymerase II core promoter: a key component in the regulation of gene expression," Genes & Dev., 2002, 16:2583-2592.
Canadian Office Action in Canadian Application No. 2907198, dated Jul. 8, 2016, 4 pages.
Carbonetti et al., "Use of pertussis toxin vaccine molecule PT19K/129G to deliver peptide epitopes for stimulation of a cytotoxic T lymphocyte response," Abstr. Annu. Meet. Am. Soc. Microbiol., 1995, 95:295.
Carroll et al., "Design, construction and in vitro testing of zinc finger nucleases," Nat Protoc., 1(3):1329-1341, 2006.
Carroll, "A CRISPR Approach to Gene Targeting," Molecular Therapy, 2012, 20(9):1658-1660.
Carroll, "Progress and prospects: zinc-finger nucleases as gene therapy agents," Gene Ther., 15(22):1463-1468, Epub Sep. 11, 2008.
Carroll, "Staying on target with CRISPR-Case," Nat Biotechnol., 2013, 31(9):807-809.
Castellano et al., "Inducible recruitment of Cdc42 or WASP to a cell-surface receptor triggers actin polymerization and filopodium formation," Curr. Biol., 1999, 9(7): 351-360.
Cathomen and Joung, "Zinc-finger nucleases: the next generation emerges," Mol. Ther., 2008, 16:1200-1207.
Cermak et al., "Efficient design and assembly of custom TALEN and other TAL effector-based constructs for DNA targeting," Nucleic Acids Res., 39:e82, p. 1-11 (2011).
Chaikind et al., "Targeted DNA Methylation Using an Artificially Bisected M.HhaI Fused to Zinc Fingers," PLoS ONE, 7(9):E44852 pp. 1-11 (2012).
Chang et al., "Genome editing with RNA-guided Cas9 nuclease in zebrafish embryos," Cell Res., 2013, 23:465-472.
Chen & Zhao, "A highly sensitive selection method for directed evolution of homing endonucleases," Nucleic Acids Res., 2005, 33(18):e154.
Chen et al., "Cut Site Selection by the Two Nuclease Domains of the Cas9 RNA-guided Endonuclease," J Biol Chem. May 9, 2014; 289(19):13284-94.
Chen et al., "Dynamic imaging of genomic loci in living human cells by an optimized CRISPR/Cas system," Cell, 2013, 155(7):1479-1491.
Chen et al., "Efficient genome editing in Caenorhabditis elegans by CRISPR-targeted homologous recombination," Nucleic Acids Res., 2013, 41(20):e193, 6 pages.
Chen et al., "Induced DNA demethylation by targeting Ten-Eleven Translocation 2 to the human ICAM-1 promoter," Nucleic Acids Res., 42(3):1563-1574, Epub Nov. 4, 2013.
Cheng et al., "Multiplexed activation of endogenous genes by CRISPR-on, an RNA-guided transcriptional activator system," Cell Res., Oct. 2013, 23(10):1163-71.
Chim et al., "Methylation profiling in multiple myeloma," Leuk. Res., Apr. 2004, 28:379-85.
Chiu et al., "Transgene-free genome editing in Caenorhabditis elegans using CRISPR-Cas," Genetics, Nov. 2013, 195(3):1167-71.
Cho et al., "Analysis of off-target effects of CRISPR/Case-derived RNA-guided endonucleases and nickases," Genome Res., 2014, 24:132-141.
Cho et al., "Targeted genome engineering in human cells with the Cas9 RNA-guided endonuclease," Nat Biotechnol., 2013, 31:230-232.
Choo and Klug, "Toward a code for the interactions of zinc fingers with DNA: selection of randomized fingers displayed on phage," Proc Natl Acad Sci U S A., 91(23):11163-11167, Nov. 8, 1994.
Christian et al., "Targeting DNA Double-Strand Breaks with TAL Effector Nucleases," Genetics, 2010, 186:757-761 (2010).
Chylinski et al., "Classification and evolution of type II CRISPR-Cas systems," Nucleic Acids Res. 2014;42(10):6091-105.
Chylinski et al., "The tracrRNA and Cas9 families of type II CRISPR-Cas immunity systems," RNA Biol., 2013, 10(5):726-737.
Clark-Curtiss and Curtiss, "[23] Analysis of recombinant DNA using *Escherichia coli* minicells," Methods in Enzymology, 1983, 101:347-362.
Colley et al., "Conversion of a Golgi Apparatus Sialyltransferase to a Secretory Protein by Replacement of the NH2-terminall Signal Anchor with a Signal Peptide," J. Biol. Chem., 1989, 264:17619-22.
Cong et al., "Multiplex genome engineering using CRISPR/Cas systems," Science, 2013, 339:819-823 (Author Manuscript).
Conklin, "Sculpting genomes with a hammer and chisel," Nature Methods, 2013, 10(9):839-840.
Costa et al., "REELIN and schizophrenia: a disease at the interface of the genome and the epigenome," Mol. Interv., Feb. 2002, 2:47-57.
Crabtree and Schreiber, "Three-part inventions: intracellular signaling and induced proximity," Trends Biochem. Sci., Nov. 1996, 21(11):418-422.
Cradick et al., "CRISPR/Cas9 systems targeting beta-globin and CCR5 genes have substantial off-target activity," Nucleic Acids Res., 2013, 41(20):9584-92.
D'Avignon et al., "Site-specific experiments on folding/unfolding of Jun coiled coils: thermodynamic and kinetic parameters from spin inversion transfer nuclear magnetic resonance at leucine-18," Biopolymers, 83(3):255-267, Oct. 15, 2006.
De Souza, "RNA-guided gene editing," Nat Methods, Mar. 2013, 10(3):189.
De Zhu, "The altered DNA methylation pattern and its implications in liver cancer," Cell. Res., 2005, 15:272-80.
Deltcheva et al., "CRISPR RNA maturation by trans-encoded small RNA and host factor RNAse III," Nature, 2011, 471(7340):602-607 (Author Manuscript).
Deveau et al., "Phage response to CRISPR-encoded resistance in *Streptococcus thermophilus*," J Bacteriol., Feb. 2008, 190(4):1390-400.
Dicarlo et al., "Genome engineering in *Saccharomyces cerevisiae* using CRISPR-Cas systems," Nucleic Acids Res., 2013, 41(7):4336-43.
Dickinson et al., "Engineering the Caenorhabditis elegans genome using Cas9-triggered homologous recombination," Nat Methods., Oct. 2013, 10(10):1028-34.
Ding et al., "Enhanced efficiency of human pluripotent stem cell genome editing through replacing TALENs with CRISPRs," Cell Stem Cell., Apr. 4, 2013, 12(4):393-4 (Author Manuscript).
Donnelly et al., "Targeted delivery of peptide epitopes to class I major histocompatibility molecules by a modified Pseudomonas exotoxin," PNAS, Apr. 1993, 90:3530-34.
Doudna and Charpentier, "Genome editing. The new frontier of genome engineering with CRISPR-Cas9," Science, Nov. 2014, 346:1258096, 11 pages.
Doyon et al., "Directed Evolution and Substrate Specificity Profile of Homing Endonuclease I-SceI," J. Am. Chem. Soc., 2006, 128:2477-2484.
Doyon et al., "Heritable targeted gene disruption in zebrafish using designed zinc-finger nucleases," Nat Biotechnol., Jun. 2008, 26:702-708.
Dranoff et al., "A phase I study of vaccination with autologous, irradiated melanoma cells engineered to secrete human granulocyte-macrophage colony stimulating factor," Hum. Gene Ther., Jan. 1997, 8(1):111-23.
Dunbar et al., "Retrovirally Marked CD34-Enriched Peripheral Blood and Bone Marrow Cells Contribute to Long-Tenn Engraftment After Autologous Transplantation," Blood, Jun. 1995, 85:3048-3057.

(56) References Cited

OTHER PUBLICATIONS

Eisenschmidt et al., "Developing a programmed restriction endonuclease for highly specific DNA cleavage," Nucleic Acids Res., 33(22):7039-47 (2005).
Ellem et al., "A case report: immune responses and clinical course of the first human use of granulocyte/macrophage-colony-stimulating-factor-transduced autologous melanoma cells for immunotherapy," Immunol Immunother., Mar. 1997, 44:10-20.
Elrod-Erickson et al., "High-resolution structures of variant Zif268-DNA complexes: implications for understanding zinc finger-DNA recognition," Structure, 6(4):451-464, Apr. 15, 1998.
Esteller et al., "A Gene Hypermethylation Profile of Human Cancer," Cancer Res., Apr. 2001, 61:3225-9.
Esteller et al., "Promoter Hypermethylation and BRCA1 Inactivation in Sporadic Breast and Ovarian Tumors," J. Natl. Cancer Inst., Apr. 2000, 92:564-9.
Esvelt et al., "Orthogonal Cas9 proteins for RNA-guided gene regulation and editing," Nat Methods, Nov. 2013, 10(11):1116-21.
European Partial Supplementary Search Report in European Application No. 14764117.9, dated Aug. 11, 2016, 7 pages.
European Search Report in European Application No. 14763916.5, dated Jul. 27, 2016, 10 pages.
Fisher et al., "A scalable, fully automated process for construction of sequence-ready human exome targeted capture libraries," Genome Biol., 2011, 12-R1.
Fonfara et al., "Phylogeny of Cas9 determines functional exchangeability of dual-RNA and Cas9 among orthologous type II CRISPR-Cas systems." Nucleic Acids Res., Feb. 2014, 42(4):2577-90.
Freeman et al., "Inducible Prostate Intraepithelial Neoplasia with Reversible Hyperplasia in Conditional FGFR1-Expressing Mice," Cancer Res., Dec. 2003, 63(23):8256-8563.
Friedland et al., "Heritable genome editing in C. elegans via a CRISPR-Cas9 system," Nature Methods 10(8): 741-743, 2013 (Author Manuscript).
Fu et al, Targeted genome editing in human cells using CRISPR/Cas nucleases and truncated guide RNAs, Methods in Enzymology, 546: 21-45.
Fu et al., "High-frequency off-target mutagenesis induced by CRISPR-Cas nucleases in human cells," Nat Biotechnol., 2013, 31:822-826 (Author Manuscript).
Fu et al., "Improving CRISPR-Cas nuclease specificity using truncated guide RNAs," Nat. Biotechnol. Mar. 2014, 32:279-284.
Gabriel et al., "An unbiased genome-wide analysis of zinc-finger nuclease specificity," Nat Biotechnol., 2011, 29:816-823.
Gagnon et al., "Efficient mutagenesis by Cas9 protein-mediated oligonucleotide insertion and large-scale assessment of single-guide RNAs," PLoS One, May 2014, 9, e98186.
Gao et al., "Hypermethylation of the RASSF1A gene in gliomas," Clin. Chim. Acta., Nov. 2004, 349:173-9.
Garcia-Bustos et al., "Nuclear protein localization," Biochim. Biophys. Acta, Mar. 1991, 1071:83-101.
Garneau et al., "The CRISPR/Cas bacterial immune system cleaves bacteriophage and plasmid DNA," Nature, Nov. 4, 2010, 468(7320):67-71.
Gasiunas and Siksnys, "RNA-dependent DNA endonuclease Cas9 of the CRISPR system: Holy Grail of genome editing?" Trends Microbiol., 2013, 21(11):562-567.
Gasiunas, "Cas9-crRNA ribonucleoprotein complex mediates specific DNA cleavage for adaptive immunity in bacteria," Proc Natl Acad Sci U S A, Sep. 25, 2012, 109(39):E2579-86.
Geibler et al., "Transcriptional Activators of Human Genes with Programmable DNA-Specificity ," PLoS ONE, 6:e19509 (2011).
Gilbert et al., "CRISPR-mediated modular RNA-guided regulation of transcription in eukaryotes," Cell, 2013, 154(2):442-51.
Gossen and Bujard, "Tight control of gene expression in mammalian cells by tetracycline-responsive promoters," Proc. Natl. Acad. Sci., Jun. 1992, 89:5547-5551.
Graef et al., "Proximity and orientation underlie signaling by the non-receptor tyrosine kinase ZAP70," Embo. J., 1997, 16(18):5618-5628.
Gratz et al., "CRISPR/Cas9-mediated genome engineering and the promise of designer flies on demand," Fly (Austin), Oct.-Dec. 2013, 7(4):249-55.
Gratz et al., "Genome engineering of *Drosophila* with the CRISPR RNA-guided Cas9 nuclease," Genetics, 2013, 194(4):1029-35.
Grizot et al., "Generation of redesigned homing endonucleases comprising DNA-binding domains derived from two different scaffolds," Nucleic Acids Res., 38(6):2006-2018, Epub Dec. 21, 2009.
Gross and Garrard, "Nuclease Hypersensitive Sites in Chromatin," Annu. Rev. Biochem., Jul. 1988, 57:159-97.
Guilinger et al., "Broad specificity profiling of TALENs results in engineered nucleases with improved DNA-cleavage specificity," Nat. Methods, Apr. 2014, 11:429-435.
Guilinger et al., "Fusion of catalytically inactive Cas9 to FokI nuclease improves the specificity of genome modification," Nat Biotechnol., Apr. 2014, 32(6):577-583.
Guo et el., "Hydroxylation of 5-Methylcytosine by TET1 Promotes Active DNA Demethylation in the Adult Brain," Cell, 145:423-434 (2011).
Haft et al., "A Guild of 45 CRISPR-Associated (Cas) Protein Families and multiple CRISPER/cas Subtypes Exist in Prokaryotic Genomes," PLOS, 2005, 1(6):0474-0483.
Hale et al., "Essential features and rational design of CRISPR RNAs that function with the Case RAMP modlule complex to cleave RNAs," Mol Cell., 2012, 45(3):292-302 (Author Manuscript).
Han et al., "CTCF Is the Master Organizer of Domain-Wide Allele-Specific Chromatin at the H19/Igf2 Imprinted Region," Mol Cell Biol., Feb. 2008, 28(3):1124-35.
Han et al., "Ligand-directed retroviral targeting of human breast cancer cells," PNAS, Oct. 1995, 92:9747-51.
Harikrishna et al., "Construction and function of fusion enzymes of the human cytochrome P450scc system," DNA Cell Biol., 12(5):371-379, Jun. 1993.
Harrison, "A structural taxonomy of DNA-binding domains," Nature, 353(6346): 715-719, Oct. 24, 1991.
Haurwitz et al., "Sequence- and Structure-Specific RNA Processing by a CRISPR Endonuclease," Science, Sep. 2010, 329(5997):1355-8.
Haurwitz, R. "The CRISPR endoribonuclease Csy4 utilizes unusual sequence and structures pecific mechanisms to recognize and process crRNAs," Thesis. May 8, 2012 (May 8, 2012), University of California, Berkeley, pp. 1-120. Retrieved from the Internet:<http://escholarship.org/uc/item/0rh5940p> on Dec. 26, 2014 (Dec. 26, 2014). entire document.
He et al., "Tet-Mediated Formation of 5-Carboxylcytosine and Its Excision by TDG in Mammalian DNA," Science, 333:1303-1307 (2011).
Hockemeyer et al., "Genetic engineering of human ES and iPS cells using TALE nucleases," Nat Biotechnol., 2011, 29:731-734 (Author Manuscript).
Horii et al., "Generation of an ICF Syndrome Model by Efficient Genome Editing of Human Induced Pluripotent Stem Cells using the CRISPR System," Int J Mol Sci., 2013, 14:19774-19781.
Horvath and Barrangou, "CRISPR/Cas, the immune system of bacteria and archaea," Science, 2010, 327:167-170.
Horvath et al., "Diversity, activity, and evolution of CRISPR loci in *Streptococcus thermophilus*," J. Bacteriol., Feb. 2008, 190:1401-1412.
Hou et al., "Efficient genome engineering in human pluripotent stem cells using Cas9 from Neisseria meningitidis," Proc Natl Acad Sci U S A, Sep. 24, 2013, 110(39):15644-9.
Hsu et al., "Development and Applications of CRISPR-Cas9 for Genome Engineering," Cell, 2014, 157(6):1262-1278.
Hsu et al., "DNA targeting specificity of RNA-guided Cas9 nucleases," Nat Biotechnol., 2013, 31:827-832.
Huang et al., "Heritable gene targeting in zebrafish using customized TALENs," Nat. Biotechnol., 29:699-700 (2011).
Hwang et al., "Efficient In Vivo Genome Editing Using RNA-Guided Nucleases," Nat Biotechnol., 2013, 31:227-229 (Author Manuscript).
Hwang et al., "Heritable and Precise Zebrafish Genome Editing Using a CRISPR-Cas System," PLoS One, 2013, 8(7):e68708, 9 pages.

(56) References Cited

OTHER PUBLICATIONS

International Preliminary Report on Patentability in International Application No. PCT/US2013/043075, dated Dec. 2, 2014, 7 pages.
International Preliminary Report on Patentability in International Application No. PCT/US2014/027335, dated Sep. 15, 2015, 10 pages.
International Preliminary Report on Patentability in International Application No. PCT/US2014/028630, dated Sep. 15, 2015, 8 pages.
International Preliminary Report on Patentability in International Application No. PCT/US2014/029068, dated Sep. 15, 2015, 10 pages.
International Preliminary Report on Patentability in International Application No. PCT/US2014/029304, dated Sep. 22, 2015, 12 pages.
International Preliminary Report on Patentability in International Application No. PCT/US2014/056416, dated Jun. 28, 2016, 7 pages.
International Search Report and Written Opinion in International Application No. PCT/US2013/043075, dated Sep. 26, 2013, 10 pages.
International Search Report and Written Opinion in International Application No. PCT/US2014/027335, dated Jul. 16, 2014, 13 pages.
International Search Report and Written Opinion in International Application No. PCT/US2014/028630, dated Jul. 24, 2014, 9 pages.
International Search Report and Written Opinion in International Application No. PCT/US2014/029068, dated Nov. 5, 2014, 15 pages.
International Search Report and Written Opinion in International Application No. PCT/US2014/029304, dated Nov. 14, 2014, 17 pages.
International Search Report and Written Opinion in International Application No. PCT/US2014/035162, dated Oct. 14, 2014, 10 pages.
International Search Report and Written Opinion in International Application No. PCT/US2014/056416, dated Apr. 3, 2015, 11 pages.
Invitation to Pay Additional Fees and, Where Applicable, Protest Fee in International Application No. PCT/US2014/029068, dated Aug. 20, 2014, 3 pages.
Invitation to Pay Additional Fees and, Where Applicable, Protest Fee in International Application No. PCT/US2014/029304, dated Jul. 30, 2014, 3 pages.
Isalan et al., "A rapid, generally applicable method to engineer zinc fingers illustrated by targeting the HIV-1 promoter," Nat. Biotechnol., 19(7):656-660, Jul. 2001.
Ishino et al., "Nucleotide sequence of the iap gene, responsible for alkaline phosphatase isozyme conversion in *Escherichia coli*, and identification of the gene product," J Bacteriol., Dec. 1987, 169(12):5429-33.
Ito et al., "Tet proteins can convert 5-methylcytosine to 5-formylcytosine and 5-carboxylcytosine," Science, 333(6047):1300-1303, Sep. 2, 2011.
Iyer et al., "Prediction of novel families of enzymes involved in oxidative and other complex modifications of bases in nucleic acids," Cell Cycle, Jun. 1, 2009, 8(11):1698-710.
Iyer et al., Supplementary Material for "Prediction of novel families of enzymes involved in oxidative and other complex modifications of bases in nucleic acids," Cell Cycle, Jun. 1, 2009, 8(11):1698-710, [retrieved on Dec. 22, 2015]. Retrieved from the Internet: URL <ftp://ftp.ncbi.nih.gov/pub/aravind/DONS/supplementary_material_DONS.html>.
Jamieson et al., "In vitro selection of zinc fingers with altered DNA-binding specificity," Biochemistry, 33(19):5689-5695, May 17, 1994.
Jansen et al., "Identification of genes that are associated with DNA repeats in prokaryotes," Mol Microbiol., Mar. 2002, 43(6):1565-75.
Jiang et al., "CRISPR-assisted editing of bacterial genomes," Nat Biotechnol., 2013, 31:233-239 (Author Manuscript).

Jiang et al., "Structural Biology. A Cas9-guide RNA complex preorganized for target DNA recognition," Science, Jun. 2015, 348:1477-1481.
Jinek et al., "A programmable dual-RNA-guided DNA endonuclease in adaptive bacterial immunity," Science, 2012, 337:816-821.
Jinek et al., "RNA-programmed genome editing in human cells," Elife, 2013, 2:e00471, 9 pages.
Jinek et al., "Structures of Cas9 Endonucleases Reveal RNA-Mediated Conformational Activation," Science. Mar. 14, 2014; 343(6176):1247997.
Josephs et al., "Structure and specificity of the RNA-guided endonuclease Cas9 during DNA interrogation, target binding and cleavage," Nucleic Acids Res., Sep. 2015, 43:8924-8941.
Joung and Sander, "TALENs: a widely applicable technology for targeted genome editing," Nat Rev Mol Cell Biol., 14(1):49-55, Epub Nov. 21, 2012.
Joung et al., "Reply to "Successful genome editing with modularly assembled zinc finger nucleases"," Nat. Methods, Jan. 2010, 7:91-92.
Karkare and Bhatnagar, "Promising nucleic acid analogs and mimics: characteristic features and applications of PNA, LNA, and morpholino", Applied Microbiology and Biotechnology, May 2006, 71(5): 575-586.
Karmirantzou and Harnodrakas, "A Web-based classification system of DNA-binding protein families," Protein Eng. 14(7):465-472, Jul. 2001.
Karvelis et al., "crRNA and tracrRNA guide Cas9-mediated DNA interference in *Streptococcus thermophilus*," RNA Biol., 2013, 10(5):841-851.
Katie and Großhans, "Targeted heritable mutation and gene conversion by Cas9-CRISPR in Caenorhabditis elegans," Genetics, Nov. 2013, 195(3):1173-6.
Kearns et al., "Recombinant adeno-associated virus (AAV-CFTR) vectors do not integrate in a site-specific fashion in an immortalized epithelial cell line," Gene Ther., Sep. 1996, 9:748-55.
Keryer-Bibens et al., "Tethering of proteins to RNAs by bacteriophage proteins," Biol Cell, 2008, 100:125-138.
Kiani et al., "Cas9 gRNA engineering for genome editing, activation and repression," Nat. Methods, 2015, 12:1051-1054.
Kim and Kim, "A guide to genome engineering with programmable nucleases," Nature Rev Genetics 15, 321-334 (2014).
Kim et al., "Highly efficient RNA-guided genome editing in human cells via delivery of purified Cas9 ribonucleoproteins," Genome Res. Jun. 2014; 24(6):1012-9.
Kim et al., "Targeted genome editing in human cells with zinc finger nucleases constructed via modular assembly," Genome Res., 19(7):1279-1288, Epub May 21, 2009.
Kim et al., "Genome editing with modularly assembled zinc-finger nucleases," Nat. Methods, 7(2):91-92, Feb. 2010.
Kleinstiver et al., "A unified genetic, computational and experimental framework identifies functionally relevant residues of the homing endonuclease I-BmoI," Nucleic Acids Res., 2010, 38:2411-2427.
Kleinstiver et al., "Engineered CRISPR-Cas9 nucleases with altered Pam specificities," Nature, Jul. 2015, 523(7561):481-5.
Klimpel et al., "Anthrax toxin protective antigen is activated by a cell surface protease with the sequence specificity and catalytic properties of furin," PNAS, Nov. 1992, 89:10277-81.
Klug, "Co-chairman's remarks: protein designs for the specific recognition of DNA," Gene, 135(1-2):83-92, Dec. 15, 1993.
Koike-Yusa et al., "Genome-wide recessive genetic screening in mammalian cells with a lentiviral CRISPR-guide RNA library," Nat Biotechnol., Mar. 2014, 32(3):267-73.
Kondo and Ueda, "Highly improved gene targeting by germline-specific Cas9 expression in *Drosophila*," Genetics, Nov. 2013, 195(3):715-21.
Konermann et al., "Optical control of mammalian endogenous transcription and epigenetic states," Nature. Aug. 22, 2013; 500(7463):472-6. (Author Manuscript).
Kumar et al., "DNA-Prot: identification of DNA binding proteins from protein sequence information using random forest," J Biomol Struct Dyn., 26(6):679-686, Jun. 2009.

(56) References Cited

OTHER PUBLICATIONS

Kumar et al., "Identification of DNA-binding proteins using support vector machines and evolutionary profiles," BMC Bioinformatics, 8:463, Nov. 27, 2007.

Kummerfeld and Teichmann, "DBD: a transcription factor prediction database," Nucleic Acids Res., 34 (Database issue): D74-D81, Jan. 1, 2006.

Kurmasheva et al., "Upstream CpG island methylation of the PAX3 gene in human rhabdomyosarcomas," Pediatr. Blood Cancer, Apr. 2005, 44:328-37.

Lea et al., "Aberrant p16 methylation is a biomarker for tobacco exposure in cervical squamous cell carcinogenesis," Am. J. Obstet. Gynecol., 2004, 190:674-9.

Lee et al., "Three-dimensional solution structure of a single zinc finger DNA-binding domain," Science., 245(4918):635-637, Aug. 11, 1989.

Li et al., "DNA methylation in prostate cancer," Biochim. Biophys. Acta, Sep. 2004, 1704:87-102.

Li et al., "Heritable gene targeting in the mouse and rat using a CRISPR-Cas system," Nat Biotechnol, Aug. 2013, 31(8):681-3.

Li et al., "Modularly assembled designer TAL effector nucleases for targeted gene knockout and gene replacement in eukaryotes," Nucleic Acids Res., 39(14):6315-6325, Epub Mar. 31, 2011.

Li et al., "Protein trans-splicing as a means for viral vector-mediated in vivo gene therapy," Hum Gene Ther., 19(9):958-964, Sep. 2008.

Li et al., "Simultaneous generation and germline transmission of multiple gene mutations in rat using CRISPR-Cas systems," Nat Biotechnol., Aug. 2013, 31(8):684-6.

Li et al., "TAL nucleases (TALNs): hybrid proteins composed of TAL effectors and FokI DNA-cleavage domain," Nucleic Acids Res., 2011, 39(1): 359-372.

Lin et al., "CRISPR/Cas9 systems have off-target activity with insertions or deletions between target DNA and guide RNA sequences," Nucleic Acids Res., 2014, 42:7473-7485.

Lin et al., "iDNA-Prot: identification of DNA binding proteins using random forest with grey model," PLoS One., 6(9):e24756, Epub Sep. 15, 2011.

Liu et al., "Regulation of an Endogenous Locus Using a Panel of Designed Zinc Finger Proteins Targeted to Accessible Chromatin Regions," J. Biol. Chem., Apr. 2001, 276(14):11323-34.

Liu et al., "Validated zinc finger protein designs for all 16 GNN DNA triplet targets," J. Biol. Chem., 277(6):3850-3856, Epub Nov. 28, 2001.

Lo et al., "Precise and Heritable Genome Editing in Evolutionarily Diverse Nematodes Using TALENs and CRISPR/Cas9 to Engineer Insertions and Detections," Genetics, 2013, 195:331-348.

Lund et al., "DNA Methylation Polymorphisms Precede Any Histological Sign of Atherosclerosis in Mice Lacking Apolipoprotein E," J. Biol. Chem., Jul. 2004, 279:29147-54.

Mabaera et al., "Developmental- and differentiation-specific patterns of human γ- and β-globin promoter DNA methylation," Blood, 110(4):1343-52 (2007).

Maeder et al., "CRISPR RNA-guided activation of endogenous human genes," Nat Methods, 2013, 10:977-979 (Author Manuscript).

Maeder et al., "Rapid 'open-source' engineering of customized zinc-finger nucleases for highly efficient gene modification," Mol Cell, 2008, 31(2):294-301.

Maeder et al., "Robust, synergistic regulation of human gene expression using TALE activators," Nat. Methods, 2013, 10:243-245.

Maeder et al., "Targeted DNA demethylation and activation of endogenous genes using programmable TALE-TET1 fusion proteins," Nat Biotechnol., 31(12):1137-1142, [author manuscript] Epub Oct. 9, 2013.

Mahfouz et al., "De novo-engineered transcription activator-like effector (TALE) hybrid nuclease with novel DNA binding specificity creates double-strand breaks," Proc Natl Acad Sci U S A, 108:2623-2628 (2011).

Maiti and Drohat, "Thymine DNA glycosylase can rapidly excise 5-formylcytosine and 5-carboxylcytosine: potential implications for active demethylation of CpG sites," J Biol Chem., 286(41):35334-35338, Epub Aug. 23, 2011.

Majumdar et al., "Targeted Gene Knock in and Sequence Modulation Mediated by a Psoralen-linked Triplex-forming Oligonucleotide," J Biol Chem., 283(17):11244-52 (2008).

Makarova et al., "A putative RNA-interference-based immune system in prokaryotes: computational analysis of the predicted enzymatic machinery, functional analogies with eukaryotic RNAi, and hypothetical mechanisms of action," Biol. Direct, 2006, 1:7, 26 pages.

Makarova et al., "Evolution and classification of the CRISPR-Cas systems," Na Rev. Microbiol., 2011, 9(6):467-77 (Author Manuscript).

Makarova et al., "Unification of Cas protein families and a simple scenario for the origin and evolution of CRISPR-Cas systems," Biol. Direct, 2011, 6:38, 27 pages.

Malech et al., "Prolonged production of NADPH oxidase-corrected granulocytes after gene therapy of chronic granulomatous disease," PNAS, Oct. 1997, 94:12133-38.

Mali et al., "Cas9 as a versatile tool for engineering biology," Nature Methods, 2013, 10(10):957-963.

Mali et al., "CAS9 transcriptional activators for target specificity screening and paired nickases for cooperative genome engineering," Nat Biotechnol., 2013, 31:833-838.

Mali et al., "RNA-guided human genome engineering via Cas9," Science, Feb. 2013, 339:823-826 (Author Manuscript).

Mancini et al. "CpG methylation within the 5' regulatory region of the BRCA1 gene is tumor specific and includes a putative CREB binding site," Oncogene, 1998, 16:1161-9.

Mandell and Barbas et al., "Zinc Finger Tools: custom DNA-binding domains for transcription factors and nucleases," Nucleic Acids Res., 34(Web Server issue):W516-W523, Jul. 1, 2006.

Marraffini and Sontheimer, "CRISPR Interference Limits Horizontal Gene Transfer in Staphylococci by Targeting DNA," Sci., 2008, 322(5909):1843-1845.

Marraffini and Sontheimer, "Self vs. non-self discrimination during CRISPR RNA-directed immunity," Nature, 2010, 463(7280):568-571 (Author Manuscript).

Mashiko et al., "Generation of mutant mice by pronuclear injection of circular plasmid expressing Cas9 and single guided RNA," Sci Reports, 2013, 3(3355):1-6.

McGarty, "CRISPRs and Cancer," White Paper No. 111, Apr. 2014, 22 pages.

Mendenhall et al., "Locus-specific editing of histone modifications at endogenous enhancers," Nat Biotechnol., 31(12):1133-1136, Epub Sep. 8, 2013.

Miller et al., "A TALE nuclease architecture for efficient genome editing," Nature Biotechnology, Feb. 2011, 29:143-148.

Miller et al., "An improved zinc-finger nuclease architecture for highly specific genome editing," Nat Biotechnol., 2007, 25:778-785.

Miller et al., "Repetitive zinc-binding domains in the protein transcription factor IIIA from Xenopus oocytes," EMBO J., 4(6):1609-1614, Jun. 1985.

Miyazaki et al., "Expression vector system based on the chicken beta-actin promoter directs efficient production of interleukin-5," Gene, Jul. 1989, 79(2):269-77.

Mojica et al., "Biological significance of a family of regularly spaced repeats in the genomes of Archaea, Bacteria and mitochondria," Mol Microbiol., Apr. 2000, 36(1):244-6.

Mojica et al., "Short motif sequences determine the targets of the prokaryotic CRISPR defense system," Microbiology, 2009, 155:733-740.

Moore et al., "Design of polyzinc finger peptides with structured linkers," Proc Natl Acad Sci USA, Feb. 2001, 98:1432-1436.

Morbitzer et al., "Regulation of selected genome loci using de novo-engineered transcription activator-like effector (TALE)-type transcription factors," Proc Natl Acad Sci U S A., 107(50):21617-21622, Epub Nov. 24, 2010.

(56) References Cited

OTHER PUBLICATIONS

Morbitzer et al., "Assembly of custom TALE-type DNA binding domains by modular cloning," Nucl Acids Res., 39:5790-5799 (2011).
Morrison, "Transformation in *Escherichia coli*: Cryogenic Preservation of Competent Cells," J. Bacteriol., Oct. 1977, 132:349-351.
Moscou and Bogdanove, "A simple cipher governs DNA recognition by TAL effectors," Science, 326(5959):1501, Dec. 11, 2009.
Mussolino and Cathomen, "RNA guides genome engineering," Nat Biotechnol., 2013, 31(3):208-209.
Mussolino et al., "A novel TALE nuclease scaffold enables high genome editing activity in combination with low toxicity," Nucleic Acids Res., 2011, 39:9283-93.
Muthuswamy et al., "Controlled Dimerization of ErbB Receptors Provides Evidence for Differential Signaling by Homo- and Heterodimers," Mol. Cell. Biol., Oct. 1999, 19(10):6845-6857.
Needleman and Wunsch, "A General Method Applicable to the Search for Similarities in the Amino Acid Sequence of Two Proteins," J. Mol. Biol., 1970, 48:444-453.
Neering et al., "Transduction of Primitive Human Hematopoietic Cells With Recombinant Adenovirus Vectors," Blood, Aug. 1996, 88:1147-55.
Nishimasu et al., "Crystal structure of Cas9 in complex with guide RNA and target DNA," Cell, 2014, 156:935-949.
Nissim et al., "Multiplexed and Programmable Regulation of Gene Networks with an Integrated RNA and CRISPR/Cas Toolkit in Human Cells," Molecular Cell, May 2014, 54:698-710.
Niu et al., "Generation of gene-modified cynomolgus monkey via Cas9/RNA-mediated gene targeting in one-cell embryos," Cell, 2014, 156:836-843.
Niwa et al., "Efficient selection for high-expression transfectants with a novel eukaryotic vector," Gene, 1991, 108(2):193-9.
Novak et al., "Functional Characterization of Protease-treated Bacillus anthracis Protective Antigen," J. Biol. Chem., Aug. 1992, 267:17186-93.
Oligino et al., "Drug inducible transgene expression in brain using a herpes simplex virus vector," Gene Ther., 1998, 5:491-496.
Palva et al., "Secretion of interferon by Bacillus subtilis," Gene, 1983, 22:229-235.
Pattanayak et al., "High-throughput profiling of off-target DNA cleavage reveals RNA-programmed Cas9 nuclease specificity," Nat Biotechnol., 2013, 31:839-843 (Author Manuscript).
Pattanayak et al., "Revealing off-target cleavage specificities of zinc-finger nucleases by in vitro selection," Nat Methods, 2011, 8:765-770 (Author Manuscript).
Pavletich and Pabo, "Zinc finger-DNA recognition: crystal structure of a Zif268-DNA complex at 2.1 A," Science, 252(5007):809-817, May 10, 1991.
Perelle et al., "Characterization of Clostridium perfringens Iota-Toxin Genes and Expression in *Escherichia coli*," Infect. Immun., Dec. 1993, 61:5147-56.
Perez et al., "Establishment of HIV-1 resistance in CD4+ T cells by genome editing using zinc-finger nucleases," Nat Biotechnol., 2008, 26:808-816 (Author Manuscript).
Perez-Pinera et al., "RNA-guided gene activation by CRISPR-Case9-based transcription factors," Nat Methods, 2013, 10(10):973-976 (Author Manuscript).
Pingoud and Silva, "Precision genome surgery," Nat Biotechnol., 25(7):743-744, Jul. 2007.
Puchta and Fauser et al., "Synthetic nucleases for genome engineering in plants: prospects for a bright future," Plant J. Jun. 2014; 78(5):727-41.
Qi et al., "Repurposing CRISPR as an RNA-Guided Platform for Sequence-Specific Control of Gene Expression," Cell, Feb. 2013, 152:1173-1183.
Ramakrishna et al., "Gene disruption by cell-penetrating peptide-mediated delivery of Cas9 protein and guide RNA," Genome Res. Jun. 2014; 24(6): 1020-1027.

Ramakrishna et al., "Surrogate reporter-based enrichment of cells containing RNA-guided Cas9 nuclease-induced mutations," Nat Commun. Feb. 26, 2014; 5:3378.
Ramalingam et al., "A CRISPR way to engineer the human genome," Genome Biol., 2013, 14:107, 4 pages.
Ramirez et al., "Unexpected failure rates for modular assembly of engineered zinc fingers," Nat Methods., 5(5):374-375, May 2008.
Ran et al., "Double nicking by RNA-guided CRISPR Cas9 for enhanced genome editing specificity," Cell, 2013, 154:1380-1389.
Ran et al., "Genome engineering using the CRISPR-Cas9 system," Nature Protocols, 2013, 8(11):2281-2308.
Ran et al., "In vivo genome editing using *Staphylococcus aureus* Cas9," Nature, 2015, 520:186-191.
Rebar and Pabo, "Zinc finger phage: affinity selection of fingers with new DNA-binding specificities," Science, 263(5147):671-673, Feb. 4, 1994.
Ren et al., "Optimized gene editing technology for *Drosophila melanogaster* using germ line-specific Cas9," Proc Natl Acad Sci U S A, Nov. 19, 2013, 110(47):19012-7.
Rendahl et al., "Regulation of gene expression in vivo following transduction by two separate rAAV vectors," Nat. Biotechnol., Aug. 1998, 16:757-761.
Reyon et al., "FLASH assembly of TALENs for high-throughput genome editing," Nat Biotech, 2012, 30:460-465 (Author Manuscript).
Ro et al., "Adenovirus-based short hairpin RNA vectors containing an EGFP marker and mouse U6, human H1, or human U6 promoter," BioTechniques, 2005, 38(4):625-627.
Rodenhiser and Mann, "Epigenetics and human disease: translating basic biology into clinical applications," CMAJ, 174(3):341-348 (2006).
Rohde et al., "BISMA—Fast and accurate bisulfite sequencing data analysis of individual clones from unique and repetitive sequences," BMC Bioinformatics, 11:230 12 pages (2010).
Rothman, "Mechanisms of intracellular protein transport," Nature, 372(6501):55-63, Nov. 3, 1994.
Rusk, "CRISPRs and epigenome editing," Nature Methods, 2014, 11(1):28.
Sander and Joung et al., "CRISPR-Cas systems for editing, regulating and targeting genomes," Nat Biotechnol., Apr. 2014, 32(4):347-55.
Sander et al., "In silico abstraction of zinc finger nuclease cleavage profiles reveals an expanded landscape of off-target sites," Nucleic Acids Res., 2013, 41:e181.
Sander et al., "ZiFiT (Zinc Finger Targeter): an updated zinc finger engineering tool," Nucleic Acids Res., 2010, 38:W462-468.
Sander et al., "Zinc Finger Targeter (ZiFiT): an engineered zinc finger/target site design tool," Nucleic Acids Res., 2007, 35:W599-605.
Sander et al., "Targeted gene disruption in somatic zebrafish cells using engineered TALENs," Nat Biotechnol., 29:697-698 (2011).
Sanjana et al., A transcription activator-like effector toolbox for genome engineering, Nature Protocols, 2012, 7:171-192.
Sapranauskas et al., "The *Streptococcus thermophilus* CRISPR/Cas system provides immunity in *Escherichia coli*" Nucleic Acids Res., 2011, 39(20:9275-9282.
Schleifman et al., "Triplex-mediated gene modification," Methods Mol. Biol., 435:175-190, 2008.
Scholze & Boch, "TAL effectors are remote controls for gene activation," J. Curr. Opin. Microbiol, 14:47-53 (2011).
Schwank et al., "Functional repair of CFTR by CRISPR/Cas9 in intestinal stem cell organoids of cystic fibrosis patients," Cell Stem Cell, Dec. 5, 2013, 13(6):653-8.
Sebo et al., "Cell-invasive activity of epitope-tagged adenylate cyclase of Bordetella pertussis allows in vitro presentation of a foreign epitope to CD8+ cytotoxic T cells," Infect. Immun., Oct. 1995, 63:3851-57.
Segal et al., "Evaluation of a modular strategy for the construction of novel polydactyl zinc finger DNA-binding proteins," Biochemistry, 42(7):2137-2148, Feb. 25, 2003.
Shah et al., "Protospacer recognition motifs," RNA Biol., 2013, 10:891-899.

(56) References Cited

OTHER PUBLICATIONS

Sharma, "Schizophrenia, epigenetics and ligand-activated nuclear receptors: a framework for chromatin therapeutics," Schizophr. Res., Jan. 2005, 72:79-90.
Shen et al., "Efficient genome modification by CRISPR-Cas9 nickase with minimal off-target effects," Nat Methods, 2014, 11(4):399-402.
Shen et al., "Generation of gene-modified mice via Cas9/RNA-mediated gene targeting," Cell Res., 2013, 23(5):720-3.
Shmakov et al., "Discovery and Functional Characterization of Diverse Class 2 CRISPR-Cas Systems," Molecular Cell, 2015 60:385-397.
Silva et al., "Meganucleases and other tools for targeted genome engineering: perspectives and challenges for gene therapy," Curr Gene Ther., 11(1):11-27, Feb. 2011.
Silver, "How Proteins Enter the Nucleus," Cell, 64(3):489-497, Feb. 8, 1991.
Simon et al., "Sequence-specific DNA cleavage mediated by bipyridine polyamide conjugates," Nucl. Acids Res., 36(11):3531-8 (2008).
Stenmark et al., "Peptides fused to the amino-terminal end of diphtheria toxin are translocated to the cytosol," J. Cell Biol., Jun. 1991, 113:1025-32.
Sterman et al., "Adenovirus-mediated herpes simplex virus thymidine kinase/ganciclovir gene therapy in patients with localized malignancy: results of a phase I clinical trial in malignant mesothelioma," Hum. Gene Ther., May 1998, 7:1083-89.
Sternberg et al., "Conformational control of DNA target cleavage by CRISPR—Cas9" Nature, 2015, 527:110-113.
Sternberg et al., "DNA interrogation by the CRISPR RNA-guided endonuclease Cas9," Nature, 2014, 507:62-67.
Sternberg et al., "Mechanism of substrate selection by a highly specific CRISPR endoribonuclease," RNA, 2012, 18:661-672.
Stoddard, "Homing endonuclease structure and function," Q. Rev. Biophys., 38(1): 49-95, Epub Dec. 9, 2005.
Storrs, "A CRISPR Fore-Cas-t: A newcomer's guide to the hottest gene-editing tool on the block," Scientist Magazine, Mar. 2014, 4 pages.
Sugimoto et al., "Thermodynamic parameters to predict stability of RNA/DNA hybrid duplexes," Biochemistry, 1995, 34:11211-11216.
Sugimoto et al., "Thermodynamics-structure relationship of single mismatches in RNA/DNA duplexes," Biochemistry, Sep. 19, 2000, 39(37):11270-81.
Swarts el al., "CRISPR Interference Directed Strand Specific Spacer Acquisition," PLOS, 2012, 7(4):1-7.
Szczepek et al., "Structure-based redesign of the dimerization interface reduces the toxicity of zinc-finger nucleases," Nat Biotechnol., 2007, 25:786-793.
Szyf et al., "DNA methylation and breast cancer," Biochem. Pharmacol., Sep. 2004, 68:1187-97.
Tahiliani et al., "Conversion of 5-Methylcytosine to 5-Hydrexymethylcytosine in Mammalian DNA by MLL Partner TET1," Science, 324:930-935 (2009).
Tan et al., "Efficient nonmeiotic allele introgression in livestock using custom endonucleases," Proc Natl Acad Sci U S A, Oct. 8, 2013, 110(41):16526-31.
Tan et al., "Zinc-finger protein-targeted gene regulation: genomewide single-gene specificity," Proc Natl Acad Sci U S A., 100(21):11997-2002, Epub Sep. 26, 2003.
Terns and Terns, "CRISPR-based adaptive immune systems," Curr Opin Microbiol., 2011, 14:321-327.
Tesson et al., "Knockout rats generated by embryo microinjection of TALENs," Nat. Biotechnol., 29:695-696 (2011).
Tjong and Zhou, "DISPLAR: an accurate method for predicting DNA-binding sites on protein surfaces," Nucleic Acids Res., 35(5):1465-1477, Epub Feb. 6, 2007.
Tsai et al., "Dimeric CRISPR RNA-guided FokI nucleases for highly specific genome editing," Nat Biotechnol., Apr. 2014, 32(6):569-576.
Tsai et al., "GUIDE-Seq enables genome-wide profiling of off-target cleavage by CRISPR-Cas nucleases," Nat Biotechnol, Feb. 2015, 33:187-197.
Tzur et al., "Heritable Custom Genomic Modifications in Caenorhabdits elegans via a CRISPR-Cas9496' System," Genetics, 2013, 195:1181-1185.
Uhlmann et al., "Distinct methylation profiles of glioma subtypes," Int. J. Cancer, Aug. 2003, 106:52-9.
U.S. Final Office Action in U.S. Appl. No. 13/838,520, dated Jul. 15, 2015, 35 pages.
U.S. Final Office Action in U.S. Appl. No. 14/211,117, dated Jun. 30, 2016, 26 pages.
U.S. Non-Final Office Action in U.S. Appl. No. 14/211,117, dated Sep. 8, 2015, 20 pages.
U.S. Non-Final Office Action in U.S. Appl. No. 14/213,479, dated Dec. 9, 2015, 39 pages.
U.S. Non-Final Office Action in U.S. Appl. No. 14/213,723, dated Mar. 2, 2016, 39 pages.
U.S. Non-Final Office Action in U.S. Appl. No. 13/838,520, dated Oct. 6, 2014, 38 pages.
Van der Oost et al., "Unravelling the Structural and Mechanistic Basis of CRISPR-Cas Systems," Nature Reviews Microbiology, 2014, 12:479-492.
Ventura et al., "Cre-lox-regulated conditional RNA interference from transgenes," PNAS, Jul. 2004, 101:10380-10385.
Waaigers et al., "CRISPR/Cas9-Targeted Mutagenesis in Caenorhabditis elegant," Genetics, 2013, 195:1187-1191.
Wagner et al., "Efficient and persistent gene transfer of AAV-CFTR in maxillary sinus," Lancet, Jun. 1998, 351:1702-1703.
Wang et al., "One-Step Generation of Mice Carrying Mutations in Multiple Genes by CRISPR/Cas-Mediated Genome Engineering," Cell, 2013, 153:910-918.
Wang et al., "Positive and negative regulation of gene expression in eukaryotic cells with an inducible transcriptional regulator," Gene Ther., May 1997, 4:432-441.
Wang et al., "The CRISPR/Cas system mediates efficient genome engineering in Bombyx mori," Cell Res., Dec. 2013, 23(12):1414-6.
Weber et al., "Assembly of Designer TAL Effectors by Golden Gate Cloning," PLoS ONE, 6:e19722 (2011).
Widschwendter and Jones, "DNA methylation and breast carcinogenesis," Oncogene, Aug. 2002, 21:5462-82.
Wiedenheft, "RNA-guided genetic silencing systems in bacteria and archaea," Nature, 2012, 482:331-338.
Wolfe et al., "DNA recognition by Cys2His2 zinc finger proteins," Annu Rev Biophys Biomol Struct. 29:183-212 (2000).
Wong et al., "Detection of aberrant p16 methylation in the plasma and serum of liver cancer patients," Cancer Res., 59(1):71-73 Jan. 1, 1999.
Wood et al., "Targeted Genome Editing Across Species Using ZFNs and TALENs," Science, 333:307 (2011).
Wright et al., "Standardized reagents and protocols for engineering zinc finger nucleases by modular assembly," Nat Protoc., 2006, 1(3):1637-1652.
Wu et al., "Building zinc fingers by selection: toward a therapeutic application," Proc Natl Acad Sci U S A., 92(2):344-348, Jan. 17, 1995.
Wu et al., "Correction of a genetic disease in mouse via use of CRISPR-Cas9," Cell Stem Cell., Dec. 5, 2013, 13(6):659-62.
Wu et al., "Custom-designed zinc finger nucleases: what is next?" Cell Mol Life Sci., 64(22):2933-2944, Nov. 2007.
Wu et al., "Genome-wide binding of the CRISPR endonuclease Cas9 in mammalian cells," Nat Biotechnol. Jul. 2014; 32(7):670-6.
Xu et al., "Optimization of transcriptional regulatory elements for constructing plasmid vectors," Gene. Jul. 2001, 272(1-2):149-56.
Xu et al., "Genome-wide regulation of 5hmC, 5mC, and gene expression by Tet1 hydroxylase in mouse embryonic stem cells," Mol CELL., 42(4):451-464, Epub Apr. 21, 2011.
Yang et al., "One-step generation of mice carrying reporter and conditional alleles by CRISPR/Cas-mediated genome engineering," Cell, Sep. 12, 2013; 154(6):1370-9.
Yang et al., "Optimization of scarless human stem cell genome editing," Nucleic Acids Res., 2013, 41:9049-9061.
Yin et al., "Genome editing with Cas9 in adult mice corrects a disease mutation and phenotype," Nature Biotechnology 32, 551-553 (2014).

(56) References Cited

OTHER PUBLICATIONS

Zetsche et al., "Cpf1 Is a Single RNA-Guided Endonuclease of a Class 2 CRISPR-Cas System," Cell, 2015, 163:759-771.
Zhang et al., "Efficient construction of sequence-specific TAL effectors for modulating mammalian transcription," Nat Biotechnol., 29(2):149-153, Epub Jan. 19, 2011.
Zhang et al., "TET1 is a DNA-binding protein that modulates DNA methylation and gene transcription via hydroxylation of 5-methylcytosine," Cell Res., 20(12):1390-1393, Epub Nov. 16, 2010.
Zhou et al., "High-throughput screening of a CRISPR/Cas9 library for functional genomics in human cells," Nature. May 22, 2014; 509(7501):487-91.
Zitzewitz et al., "Probing the folding mechanism of a leucine zipper peptide by stopped-f1A4:A48ism spectroscopy," Biochemistry, 34(39):12812-12819, Oct. 3, 1995.
BLAST sequence alignment: Query = Applicants SEQ ID No. 26 and Subject = Jinek et al.'s SEQ ID No. 8 from W02013176772 (Retrieved from the Internet <https://blast.nchi.nlm.nih.gov/Blast.cgi>, retrieved on Feb. 1, 2018, 3 pages.
Farboud and Meyer, "Dramatic Enhancement of Genome Editing by CRISPR/Cas9 Through Improved Guide RNA Design," Genetics, 2015, 199:959-971.
Fu et al, "Targeted genome editing in human cells using CRISPR/Cas nucleases and truncated guide RNAs," Methods in Enzymology, Nov. 2014, 546: 21-45.
International Preliminary Report on Patentability in International Application No. PCT/US2016/49147, dated Mar. 6, 2018.
Jiang et al., "RNA-guided editing of bacterial genomes using CRISPR-Cas systems," Nature Biotechnology, Mar. 2013, 31: 233-239.
Ma et al., "A Guide RNA Sequence Design Platform for the CRISPR/Cas9 System for Model Organism Genomes," BioMed Research International, 2013, 2013: 270805, 4 pages.
Office Action in Canadian Application No. 2907198, dated May 14, 2018, 3 pages.
Office Action in Chinese Application No. 201480026133.4, dated Feb. 12, 2018, 22 pages (with English tmnslation).
Office Action in Chinese Application No. 201480026276.5, dated Apr. 17, 2018, 12 pages (with English tmnslation).
Office Action in Chinese Application No. 201480027950.1, dated Mar. 23, 2018, 13 pages (with English tmnslation).
Office Action in European Application No. 14763916.5, dated Oct. 26, 2017, 5 pages.
Office Action in European Application No. 14764117.9, dated Jan. 4, 2018, 4 pages.
Office Action in European Application No. 14764159.1, dated Nov. 21, 2017, 3 pages.
Office Action in European Application No. 14768877.4, dated Jan. 8, 2018, 4 pages.
Office Action in Japanese Application No. 2016-502976, dated May 8, 2018, 16 pages (with English translation).
Office Action in U.S. Appl. No. 14/211,117, dated Jan. 9, 2017, 12 pages.
Office Action in U.S. Appl. No. 14/211,117, dated Nov. 3, 2017, 11 pages.
Office Action in U.S. Appl. No. 14/211,117, dated Sep. 8, 2015, 20 pages.
Office Action in U.S. Appl. No. 14/775,869, dated Sep. 11, 2017, 43 pages.
Kim et al., Hybrid restriction enzymes: zinc finger fusions to Fok I cleavage domain, PNAS, Feb. 1996, 93: 1156-1160.
Melo et al., "eRNAs Are Required for p53-Dependent Enhancer Activity and Gene Transcription," Mol Cell, Feb. 2013, 49: 524-535.
Mino et al., "Efficient double-strand DNA cleavage by artificial zinc-finger nucleases composed of one zinc-finger protein and a single-chain FokI dimer," Journal of biotechnology, 2009, 140: 156-161.
Office Action in Japanese Application No. 2016-502406, dated Jun. 12, 2018, 23 pages (with English translation).
Office Action in Japanese Application No. 2016-502853, dated Jun. 12, 2018, 15 pages (with English translation).
Qi et al., "Repurposing CRISPR as an RNA-Guided Platform for Sequence-Specific Control of Gene Expression," Supplemental Information, Cell, Feb. 2013, 152.
Williams et al., Tet1 and hydroxymethylcytosine in transcription and DNA methylation fidelity, Nature, May 2011, 473: 343-349.
Nielsen et al., "Interaction with members of the heterochromatin protein 1 (HP1) family and histone deacetylation are differentially involved in transcriptional silencing by members of the TIF1 family," EMBO J., 1999, 18: 6385-6395.
Office Action in Australian Application No. 2017204909, dated Aug. 8, 2018, 8 pages.
Office Action in Chinese Application No. 201480027950.1, dated Oct. 18, 2018, 6 pages.
Office Action in European Application No. 14764117.9, dated Oct. 5, 2018, 6 pages.
Office Action in European Application No. 14875819.6, dated Jun. 19, 2018, 5 pages.
Office Action in Israeli Application No. 241671, dated Sep. 13, 2018, 8 pages (with English translation).
Office Action in Japanese Application No. 2016-542968, dated Sep. 18, 2018 (with English translation).
Ui-Tei et al., "Functional dissection of siRNA sequence by systematic DNA substitution: modified siRNA with a DNA seed arm is a powerful tool for mammalian gene silencing with significantly reduced off-target effect," Nucleic Acids Research, 2008, 36: 2136-2151.
Lino et al, "Delivering CRISPR: a review of the challenges and approaches," Drug Delivery, 2018, 25: 1234-1257.
Liu et al, "Delivery strategies of the CRISPR-Cas9 gene-editing system for therapeutic applications," Journal of Controlled Release, 2017, 266: 17-26.
Extended European Search Report in Application No. 18208105.9, dated Jan. 15, 2019, 10 pages.
Office Action in Chinese Application No. 201480076396.6, dated Feb. 19, 2019, 16 pages (with English translation).
Partial Supplementary Search report in European Application No. 16842722.7, dated Mar. 7, 2019, 13 pages.
EP Extended European Search Report in European Appln. No. 16842722.7, dated Jun. 7, 2019, 13 pages.
JP Office Action in Japanese Appln. No. 2016-502406, dated May 31, 2019, 24 pages (with English translation).
JP Office Action in Japanese Appln. No. 2016-502853, dated May 29, 2019, 7 pages (with English translation).
JP Office Action in Japanese Appln. No. 2016-542968, dated Jul. 30, 2019, 8 pages (with English translation).
Office Action in Japanese Application No. 2016-502976, dated Apr. 2, 2019, 15 pages (with English translation).

\* cited by examiner

```
Site 2    GCCGAGGTGAAGTTCGAGGGCGAC  SEQ ID NO: 26
Site 3    CCTACGGCGTGCAGTGCTTCAGC   SEQ ID NO: 27
(site S3/2)
```

```
SEQ ID NO: 55        ACGTAAACGGCCACAAGTTCAGCGTGTCCGGCGAGGGCGAGGGCGATGCCACCTACGGCAAGCTGACCCT
SEQ ID NO: 56   A1                       GTCCGGCGAGGGCGAGGGCGATGCCACCTACGGCAAGCTGACCCT
SEQ ID NO: 57   A2                        TCCGGCGAGGGCGAGGGCGATGCCACCTACGGCAAGCTGACCCT
SEQ ID NO: 58   A12                       TCCGGCGAGGGCGAGGGCGATGCCACCTACGGCAAGCTGACCCT
SEQ ID NO: 59   B12                        CCGGCGAGGGCGAGGGCGATGCCACCTACGGCAAGCTGACCCT
SEQ ID NO: 60   C3                        TCCGGCGAGGGCGAGGGCGATGCCACCTACGGCAAGCTGACCCT
SEQ ID NO: 61   C4GTAAACGGCCACAAGTTCAGCGTG---------------------------------------------
SEQ ID NO: 62   C8          CCACAAGTTCAGCGTGTCCGGCGAGGGCGAGGGCGATGCCACCTACGGCAAGCTGACCCT
SEQ ID NO: 63   D2             GGCCACAAGTTCAGCGTGTCCGGCGAGGGCGAGGGCGATGCCACCTACGGCAAGCTGACCCT
SEQ ID NO: 64   D4    TAAACGGCCACAAGTTCAGCGTGTCCGGCGAGGGCGAGGGCGATGCCACCTACGGCAAGCTGACCCT
SEQ ID NO: 65   D12            CACAAGTTCAGCGTGTCCGGCGAGGGCGAGGGCGATGCCACCTACGGCAAGCTGACCCT
SEQ ID NO: 66   E5    TAAACGGCCACAAGTTCAGCGTGTCCGGCGAGGGCGAGGGCGATGCCACCTACGGCAAGCTGACCCT
SEQ ID NO: 67   G1      AAACGGCCACAAGTTCAGCGTGTCCGGCGAGGGCGAGGGCGATGCCACCTACGGCAAGCTGACCCT
SEQ ID NO: 68   G7       ACGGCCACAAGTTCAGCGTGTCCGGCGAGGGCGAGGGCGATGCCACCTACGGCAAGCTGACCCT
SEQ ID NO: 69   G9      AAACGGCCACAAGTTCAGCGTGTCCGGCGAGGGCGAGGGCGATGCCACCTACGGCAAGCTGACCCT
SEQ ID NO: 70   G12     AAACGGCCACAAGTTCAGCGTGTCCGGCGAGGGCGAGGGCGATGCCACCTACGGCAAGCTGACCCT

SEQ ID NO: 55 CONT.   GAAGTTCATCTGCACCACCGGCAAGCTGCCCGTGCCCTGGCCCACCCTCGTGACCACCCTGACCTACGGC
SEQ ID NO: 56 CONT.   GAAGTTCATCTGCACCACCGGCAAGCTGCCCGTGCCCTGGCCCACCCTCGTGACCACCCTGACCTACGGC
SEQ ID NO: 57 CONT.   GAAGTTCATCTGCACCACCGGCAAGCTGCCCGTGCCCTGGCCCACCCTCGTGACCACCCTGAC--------
SEQ ID NO: 58 CONT.   GAAGTTCATCTGCACCACCGGCAAGCTGCCCGTGCCCTGGCCCACCCTCGTGAACACCCTGACCTACG---
SEQ ID NO: 59 CONT.   GAAGTTCATCTGCACCACCGGCAAGCTGCCCGTGCCCTGGCCCACCCTCGTGACCACCCTGACCTACG---
SEQ ID NO: 60 CONT.   GAAGTTCATCTGCACCACCGGCAAGCTGCCCGTGCCCTGGCCCACCCTCGTGACCACCCTGACCTACGG-
---------------------------------------------------------------------------------------
SEQ ID NO: 62 CONT.   GAAGTTCATCTGCACCACCGGCAAGCTGCCCGTGCCCTGGCCCACCCTCGTGACCACCCTGACCTACGGC
SEQ ID NO: 63 CONT.   GAAGTTCATCTGCACCACCGGCAC----------------------------------------------
SEQ ID NO: 64 CONT.   GAAGTTCATCTGCACCACCGGCAAGCTGCCCGTGCCCTGGCCCACCCTCGTGACCACCCTGACCTACGGC
SEQ ID NO: 65 CONT.   GAAGTTCATCTGCACCACCGGCAAGCTGCCCGTGCCCTGGCCCACCCTCGTGACCACCCTGACCTACGGC
SEQ ID NO: 66 CONT.   GAAGTTCATCTGCACCACCGGCAAGCTGCCCGTGCCCTGGCCCACCCTCGTGACCACCCTGACCTACGGC
SEQ ID NO: 67 CONT.   GAAGTTCATCTGCACCACCGGCAAGCTGCCCGTGCCCTGGCCCACCCTCGTGACCACCCTGACCTACG---
SEQ ID NO: 68 CONT.   GAAGTTCATCTGCACCACCGGCAAGCTGCCCGTGCCCTGGCCCACCCTCGTGACCACCCTGACCTACG---
SEQ ID NO: 69 CONT.   GAAGTTCATCTGCACCACCGGCAAGCTGCCCGTGCCCTGGCCCACCCTCGTGACCACCCTGACCTACG---
SEQ ID NO: 70 CONT.   GAAGTTCATCTGCACCACCGGCAAGCTGCCCGTGCCCTGGCCCACCCT----------------------
```

FIG. 5A

SEQ ID NO: 55 CONT. GTGCAGTGCTTCAGCCGCTACCCCGACCACATGAAGCAGCACGACTTCTTCAAGTCCGCCATGCCCGAAG
SEQ ID NO: 56 CONT. GTGCAGTGCTTCAGCCGCTACCCCGACCACATGAAGCAGCACGACTTCTTCAAGTCCGCCATGCCCGAAG
SEQ ID NO: 57 CONT. ---------------------------------------------------------------------
SEQ ID NO: 58 CONT. -TGCAGTGCTTCAGCCGCTACCCCGACCACATGAAGCAGCACGACTTCTTCAAGTCCGCCATGCCCGAAG
SEQ ID NO: 59 CONT. -TGCAGTGCTTCAGCCGCTACCCCGACCACATGAAGCAGCACGACTTCTTCAAGTCCGCCATGCCCGAAG
SEQ ID NO: 60 CONT. ---------------------------------------------------------------------
SEQ ID NO: 61 CONT. ---CAGTGCTTCAGCCGCTACCCCGACCACATGAAGCAGCACGACTTCTTCAAGTCCGCCATGCCCGAAG
SEQ ID NO: 62 CONT. GTGCAGTGCTTCAGCCGCTACCCCGACCACATGAAGCAGCACGACTTCTTCAAGTCCGCCATGCCCGAAG
SEQ ID NO: 63 CONT. ---------------------------------------------------------------------
SEQ ID NO: 64 CONT. GTGCAGTGCTTCAGCCGCTACCCCGACCACATGAAGCAGCACGACTTCTTCAAGTCCGCCATGCCCGAAG
SEQ ID NO: 65 CONT. GTGCAGTGCTTCAGCCGCTACCCCGACCACATGAAGCAGCACGACTTCTTCAAGTCCGCCATGCCCGAAG
SEQ ID NO: 66 CONT. GTGCAGTGCTTCAGCCGCTACCCCGACCACATGAAGCAGCACGACTTCTTCAAGTCCGCCATGCCCGAAG
SEQ ID NO: 67 CONT. -TGCAGTGCTTCAGCCGCTACCCCGACCACATGAAGCAGCACGACTTCTTCAAGTCCGCCATGCCCGAAG
SEQ ID NO: 68 CONT. ---------------------------------------------------------------------
SEQ ID NO: 69 CONT. ---------------------------------------------------------------------
SEQ ID NO: 70 CONT. ------------------------------------------------TCCGCCATGCCCGAAG

SEQ ID NO: 55 CONT. GCTACGTCCAGGAGCGCACCATCTTCTTCAAGGACGACGGCAACTACAAGACCCGCGCCGAGGTGAAGTT
SEQ ID NO: 56 CONT. GCTACGTCCAGGAGCGCACCATCTTCTTCAAGGACGACGGCAACTACAAGACCCGCG------------T
SEQ ID NO: 57 CONT. ---------------------------------------------------------------------
SEQ ID NO: 58 CONT. GCTACGTCCAGGAGCGCACCATCTTCTTCAAGGACGACGGCAACTACAAG------------------TT
SEQ ID NO: 59 CONT. GCTACGTCCAGGAGCGCACCATCTTCTTCAAGGACGACGGCAACTACAAGACCCGCGCCGAGGTGAAGTT
SEQ ID NO: 60 CONT. ---------------------------------------------------------------------
SEQ ID NO: 61 CONT. GCTACGTCCAGGAGCGCACCATCTTCTTCAAGGACGACGGCAACTACAAGAC-----GGCAACTACAAGTT
SEQ ID NO: 62 CONT. GCTACGTCCAGGAGCGCACCATCTTCTTCAAGGACGACGGCAACTACAAGAC-----------------
SEQ ID NO: 63 CONT. ------------------------CATCAAGGACGACGGCAACTACAAGACCCGCGCCGA-----AGTT
SEQ ID NO: 64 CONT. GCTACGTCCAGGAGCGCACCATCTTCTTCAAGGACGACGGCAACTACAAGACC-----------------
SEQ ID NO: 65 CONT. GCTACGTCCAGGAGCGCACCATCTTCTTCAAGGACGACGGCAACTACAAGACCCGCGCCGAGGT-----T
SEQ ID NO: 66 CONT. GCTACGTCCAGGAGCGCACCATCTTCTTCAAGGACGACGGCAACTACAAGACCCGCGCCGAGG-------
SEQ ID NO: 67 CONT. GCTACGTCCAGGAGCGCACCATCTTCTTCAAGGACGACGGCAACTACAAGACCCGCGCCGAGGTGAAGTT
SEQ ID NO: 68 CONT. -----------------------------------------------------------TGAAGTT
SEQ ID NO: 69 CONT. -----------------------------------------------------------TGAAGTT
SEQ ID NO: 70 CONT. GNTACGTCCAGGAGCGCACCATNTTCTTCAAGGACGACGGCAANTACAAGACCCGCGCCGA-----AGTT

FIG. 5B

| | |
|---|---|
| CGAGGGCGACACCCTGGTGAACCGCATCGAGCTGAAGGGCATCGACTTCAAG | SEQ ID NO: 55 (CONT.) |
| CGAGGGCGACACCCTGGTGAACCGCATCGAGCTGAAGGGCATCGACTTCAAG | SEQ ID NO: 56 (CONT.) |
| -GAGGGCGACACCCTGGTGAACCGCATCGAGCTGAAGGGCATCGACTTCAAG | SEQ ID NO: 57 (CONT.) |
| CGAGGGCGACACCCTGGTGAACCGCATCGAGCTGAAGGGCATCGACTTCAAG | SEQ ID NO: 58 (CONT.) |
| -----ACACCCTGGTGAACCGCATCGAGCTGAAGGGCATCGACTTCAA | SEQ ID NO: 59 (CONT.) |
| CGAGGGCGACACCCTGGTGAACCGCATCGAGCTGAAGGGC | SEQ ID NO: 60 (CONT.) |
| -------ACCGCATCGAGCTGAAGGGCATCGACTTCAA | SEQ ID NO: 61 (CONT.) |
| CGAGGGCGACACCCTGGTGAACCGCATCGAGCTGAAGGGCATCGACTTC | SEQ ID NO: 62 (CONT.) |
| ------TGGTGAACCGCATCGAGCTGAAGGGCATCGA | SEQ ID NO: 63 (CONT.) |
| CGAGGGCGACACCCTGGTGAACCGCATCGAGCTGAAGGGCATCGACTTCA | SEQ ID NO: 64 (CONT.) |
| -----GCGACACCCTGGTGAACCGCATCGAGCTGAAGGGCATCGACTTCAA | SEQ ID NO: 65 (CONT.) |
| CGAGGGCGACACCCTGGTGAACCGCATCGAGCTGAAGGGCATCGAC | SEQ ID NO: 66 (CONT.) |
| CGAGGGCGACACCCTGGTGAACCGCATCGAGCTGAAGGG | SEQ ID NO: 67 (CONT.) |
| CGAGGGCGACACCCTGGTGAACCGCATCGAGCTGAAGGG | SEQ ID NO: 68 (CONT.) |
| CGAGGGCGACACCCTGGTGAACCGCATCGAGCTGAAGG | SEQ ID NO: 69 (CONT.) |
| CGAGGGCGACACCCTGGTGAACCGCATCGAGCTGAAGGGCATCGACT | SEQ ID NO: 70 (CONT.) |

FIG. 5C eGFP Site 3

```
CACCCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCA
CACCCTGACCTACG---------------------------------------------------------------------------------------------
CACCCTGACCTACGGCGTGCAGTGCTTCAGCCGCTACCCCGACCACATGAAGCAGCACGACTTCTTCAAGTCCGCCATGCCCGAAGGCTACGTCCAGGAGCGCACCA
CACCCTGACCT---------------CAGCCGCTACCCCGACCACATGAAGCAGCACGACTTCTTCAAGTCCGCCATGCCCGAAGGCTACGTCCAGGAGCGCACCA
```

SEQ ID NO: 71
SEQ ID NO: 72
SEQ ID NO: 73
SEQ ID NO: 74 eGFP Site 2

```
TCTTCTTCAAGGACGACGGCAACTACAAGACCCGCGCCGAGGTGAAGTTCGAGGGCGACACCCTGGTG
-----------------------------------------TGAAGTTCGAGGGCGACACCCTGGT
TCTTCTTCAAGGACGACGGCAACTACAAGACCCGCGCCGAGG-----------GCGACACCCTGG
TCTTCTTCAAGGACGACGGCAACTACAAGACCCGCGCCGAGG------------CGACACCCTGGT
```

SEQ ID NO: 75
SEQ ID NO: 76
SEQ ID NO: 77

CCR5

```
TTATTATACATCGGAGCCCTGCCAAAAATCAATGTGAAGCAAATCAATGTGAAGCAAATCAATGTGAAGCAAATCAATCGCAGCCCGCTCCTGCCTCTACTCACTGGTGTTCATCTTTGGTTTTGTGGGCAACA
TTATTATACATCGGAGCCCTGCCAAAAATCAATGTGAAGCAAATCAATCGCAGCCCGCTCC------GCTCTACTCACTGGTGTTCATCTTTGGTTTTGTGGGCAACA
TTATTATACATCGGAGCCCTGCCAAAAATCAATGTGAAGCAAATCAATCGCAGCCCGC-----------------------------------------------A
TGCTGGTCATCCTTCATCCTGATAAACTGCAAAAGGCTGAAGAGCAT                     SEQ ID NO: 75
TGCTGGTCATCCT                                                       SEQ ID NO: 76
TGCTGGTCATCCTC                                                      SEQ ID NO: 77
```

FIG. 6

SEQUENCE LISTING

```
<160> NUMBER OF SEQ ID NOS: 54

<210> SEQ ID NO 1
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1
gttcactgcc gtataggcag                                                    20

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gttcactgcc gtataggcag ctaagaaa                                           28

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Ser
1

<210> SEQ ID NO 4
<211> LENGTH: 342
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent
<220> FEATURE:
<221> NAME/KEY: modified_base
<222> LOCATION: (43)..(342)
<223> OTHER INFORMATION: a, c, u or g and this region may encompass
      0-300 nucleotides wherein some positions may be absent

<400> SEQUENCE: 4
nnnnnnnnnn nnnnnnnnnn guuuuagagc uaugcuguuu ugnnnnnnnn nnnnnnnnnn        60
nnnnnnnnnn nnnnnnnnnn nnnnnnnnnn nnnnnnnnnn nnnnnnnnnn nnnnnnnnnn       120
nnnnnnnnnn nnnnnnnnnn nnnnnnnnnn nnnnnnnnnn nnnnnnnnnn nnnnnnnnnn       180
nnnnnnnnnn nnnnnnnnnn nnnnnnnnnn nnnnnnnnnn nnnnnnnnnn nnnnnnnnnn       240
nnnnnnnnnn nnnnnnnnnn nnnnnnnnnn nnnnnnnnnn nnnnnnnnnn nnnnnnnnnn       300
nnnnnnnnnn nnnnnnnnnn nnnnnnnnnn nnnnnnnnnn nn                         342

<210> SEQ ID NO 5
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u or g and this region may encompass
```

17-20 nucleotides wherein some positions may be absent

<400> SEQUENCE: 5
nnnnnnnnnn nnnnnnnnnn guuuuagagc ua                                32

<210> SEQ ID NO 6
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 6
nnnnnnnnnn nnnnnnnnnn guuuuagagc uaugcuguuu ug                     42

<210> SEQ ID NO 7
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 7
nnnnnnnnnn nnnnnnnnnn guuuuagagc uaugcu                            36

<210> SEQ ID NO 8
<211> LENGTH: 362
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent
<220> FEATURE:
<221> NAME/KEY: modified_base
<222> LOCATION: (63)..(362)
<223> OTHER INFORMATION: a, c, u or g and this region may encompass
      0-300 nucleotides wherein some positions may be absent

<400> SEQUENCE: 8
nnnnnnnnnn nnnnnnnnnn guuuuagagc uagaaauagc aaguuaaaau aaggcuaguc   60
cgnnnnnnnn nnnnnnnnnn nnnnnnnnnn nnnnnnnnnn nnnnnnnnnn nnnnnnnnnn  120
nnnnnnnnnn nnnnnnnnnn nnnnnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnnnnnnn nnnnnnnnnn nnnnnnnnnn nnnnnnnnnn  300
nnnnnnnnnn nnnnnnnnnn nnnnnnnnnn nnnnnnnnnn nnnnnnnnnn nnnnnnnnnn  360 nn                                                                 362

<210> SEQ ID NO 9

```
<211> LENGTH: 375
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent
<220> FEATURE:
<221> NAME/KEY: modified_base
<222> LOCATION: (76)..(375)
<223> OTHER INFORMATION: a, c, u or g and this region may encompass
      0-300 nucleotides wherein some positions may be absent

<400> SEQUENCE: 9
nnnnnnnnnn nnnnnnnnnn guuuuagagc uaugcugaaa agcauagcaa guuaaaauaa      60
ggcuaguccg uuaucnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnn                                                      375

<210> SEQ ID NO 10
<211> LENGTH: 387
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent
<220> FEATURE:
<221> NAME/KEY: modified_base
<222> LOCATION: (88)..(387)
<223> OTHER INFORMATION: a, c, u or g and this region may encompass
      0-300 nucleotides wherein some positions may be absent

<400> SEQUENCE: 10
nnnnnnnnnn nnnnnnnnnn guuuuagagc uaugcuguuu uggaaacaaa acagcauagc      60
aaguuaaaau aaggcuaguc cguuaucnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnn                                         387

<210> SEQ ID NO 11
<211> LENGTH: 396
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
```

```
<223> OTHER INFORMATION: a, c, u or g and this region may encompass
      17-20 nucleotides wherein some positions may be absent
<220> FEATURE:
<221> NAME/KEY: modified_base
<222> LOCATION: (97)..(396)
<223> OTHER INFORMATION: a, c, u or g and this region may encompass
      0-300 nucleotides wherein some positions may be absent

<400> SEQUENCE: 11
nnnnnnnnnn nnnnnnnnnn guuuuagagc uagaaauagc aaguuaaaau aaggcuaguc      60
cguuaucaac uugaaaaagu ggcaccgagu cggugcnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnnnnnnnn     300
nnnnnnnnnn nnnnnnnnnn nnnnnnnnnn nnnnnnnnnn nnnnnnnnnn nnnnnnnnnn     360
nnnnnnnnnn nnnnnnnnnn nnnnnnnnnn nnnnn                                396

<210> SEQ ID NO 12
<211> LENGTH: 96
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 12
nnnnnnnnnn nnnnnnnnnn guuuaagagc uagaaauagc aaguuaaaau aaggcuaguc      60
cguuaucaac uugaaaaagu ggcaccgagu cggugc                                96

<210> SEQ ID NO 13
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 13
nnnnnnnnnn nnnnnnnnnn guuuuagagc uaugcuggaa acagcauagc aaguuuaaau      60
aaggcuaguc cguuaucaac uugaaaaagu ggcaccgagu cggugc                    106

<210> SEQ ID NO 14
<211> LENGTH: 106
<212> TYPE: RNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 14
```
nnnnnnnnnn nnnnnnnnnn guuuaagagc uaugcuggaa acagcauagc aaguuuaaau    60
aaggcuaguc cguuaucaac uugaaaaagu ggcaccgagu cggugc                  106

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 15
nnnnnnnnnn nnnnnnnnnn gttttagagc tagaaa                              36

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tagcaagtta aataaggct agtccgttat caacttgaaa aagtggcacc gagtcggtgc     60

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser
1               5

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ala Tyr Pro Tyr Asp Val Pro Asp Tyr Ala Ser Leu
1               5                   10

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Pro Lys Lys Lys Arg Lys Val Glu Asp Pro Lys Lys Lys Arg Lys Val 1               5                    10                   15

Asp

<210> SEQ ID NO 20
<211> LENGTH: 1401
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe

-continued

```
                340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
                420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
```

-continued

```
Thr Thr Gln Lys Gly Gln Lys Asn Ser Arg Glu Arg Met Lys Arg Ile
    770             775             780
Glu Glu Gly Ile Lys Glu Leu Gly Ser Gln Ile Leu Lys Glu His Pro
785             790             795             800
Val Glu Asn Thr Gln Leu Gln Asn Glu Lys Leu Tyr Leu Tyr Tyr Leu
            805             810             815
Gln Asn Gly Arg Asp Met Tyr Val Asp Gln Glu Leu Asp Ile Asn Arg
            820             825             830
Leu Ser Asp Tyr Asp Val Asp His Ile Val Pro Gln Ser Phe Leu Lys
            835             840             845
Asp Asp Ser Ile Asp Asn Lys Val Leu Thr Arg Ser Asp Lys Asn Arg
850             855             860
Gly Lys Ser Asp Asn Val Pro Ser Glu Val Val Lys Lys Met Lys
865             870             875             880
Asn Tyr Trp Arg Gln Leu Leu Asn Ala Lys Leu Ile Thr Gln Arg Lys
            885             890             895
Phe Asp Asn Leu Thr Lys Ala Glu Arg Gly Gly Leu Ser Glu Leu Asp
            900             905             910
Lys Ala Gly Phe Ile Lys Arg Gln Leu Val Glu Thr Arg Gln Ile Thr
            915             920             925
Lys His Val Ala Gln Ile Leu Asp Ser Arg Met Asn Thr Lys Tyr Asp
            930             935             940
Glu Asn Asp Lys Leu Ile Arg Glu Val Lys Val Ile Thr Leu Lys Ser
945             950             955             960
Lys Leu Val Ser Asp Phe Arg Lys Asp Phe Gln Phe Tyr Lys Val Arg
            965             970             975
Glu Ile Asn Asn Tyr His His Ala His Asp Ala Tyr Leu Asn Ala Val
            980             985             990
Val Gly Thr Ala Leu Ile Lys Lys Tyr Pro Lys Leu Glu Ser Glu Phe
            995             1000            1005
Val Tyr Gly Asp Tyr Lys Val Tyr Asp Val Arg Lys Met Ile Ala
            1010            1015            1020
Lys Ser Glu Gln Glu Ile Gly Lys Ala Thr Ala Lys Tyr Phe Phe
    1025            1030            1035
Tyr Ser Asn Ile Met Asn Phe Phe Lys Thr Glu Ile Thr Leu Ala
    1040            1045            1050
Asn Gly Glu Ile Arg Lys Arg Pro Leu Ile Glu Thr Asn Gly Glu
    1055            1060            1065
Thr Gly Glu Ile Val Trp Asp Lys Gly Arg Asp Phe Ala Thr Val
    1070            1075            1080
Arg Lys Val Leu Ser Met Pro Gln Val Asn Ile Val Lys Lys Thr
    1085            1090            1095
Glu Val Gln Thr Gly Gly Phe Ser Lys Glu Ser Ile Leu Pro Lys
    1100            1105            1110
Arg Asn Ser Asp Lys Leu Ile Ala Arg Lys Lys Asp Trp Asp Pro
    1115            1120            1125
Lys Lys Tyr Gly Gly Phe Asp Ser Pro Thr Val Ala Tyr Ser Val
    1130            1135            1140
Leu Val Val Ala Lys Val Glu Lys Gly Lys Ser Lys Lys Leu Lys
    1145            1150            1155
Ser Val Lys Glu Leu Leu Gly Ile Thr Ile Met Glu Arg Ser Ser
    1160            1165            1170
```

```
Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

Ala Tyr Pro Tyr Asp Val Pro Asp Tyr Ala Ser Leu Gly Ser Gly
    1370                1375                1380

Ser Pro Lys Lys Lys Arg Lys Val Glu Asp Pro Lys Lys Lys Arg
    1385                1390                1395

Lys Val Asp
    1400

<210> SEQ ID NO 21
<211> LENGTH: 1368
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

```
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525
```

```
Tyr Val Thr Glu Gly Met Arg Lys Pro Ala Phe Leu Ser Gly Glu Gln
            530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
```

-continued

```
945                 950                 955                 960
Lys Leu Val Ser Asp Phe Arg Lys Asp Phe Gln Phe Tyr Lys Val Arg
                965                 970                 975
Glu Ile Asn Asn Tyr His His Ala His Asp Ala Tyr Leu Asn Ala Val
                    980                 985                 990
Val Gly Thr Ala Leu Ile Lys Lys Tyr Pro Lys Leu Glu Ser Glu Phe
                995                 1000                1005
Val Tyr Gly Asp Tyr Lys Val Tyr Asp Val Arg Lys Met Ile Ala
    1010                1015                1020
Lys Ser Glu Gln Glu Ile Gly Lys Ala Thr Ala Lys Tyr Phe Phe
    1025                1030                1035
Tyr Ser Asn Ile Met Asn Phe Phe Lys Thr Glu Ile Thr Leu Ala
    1040                1045                1050
Asn Gly Glu Ile Arg Lys Arg Pro Leu Ile Glu Thr Asn Gly Glu
    1055                1060                1065
Thr Gly Glu Ile Val Trp Asp Lys Gly Arg Asp Phe Ala Thr Val
    1070                1075                1080
Arg Lys Val Leu Ser Met Pro Gln Val Asn Ile Val Lys Lys Thr
    1085                1090                1095
Glu Val Gln Thr Gly Gly Phe Ser Lys Glu Ser Ile Leu Pro Lys
    1100                1105                1110
Arg Asn Ser Asp Lys Leu Ile Ala Arg Lys Lys Asp Trp Asp Pro
    1115                1120                1125
Lys Lys Tyr Gly Gly Phe Asp Ser Pro Thr Val Ala Tyr Ser Val
    1130                1135                1140
Leu Val Val Ala Lys Val Glu Lys Gly Lys Ser Lys Lys Leu Lys
    1145                1150                1155
Ser Val Lys Glu Leu Leu Gly Ile Thr Ile Met Glu Arg Ser Ser
    1160                1165                1170
Phe Glu Lys Asn Pro Ile Asp Phe Leu Glu Ala Lys Gly Tyr Lys
    1175                1180                1185
Glu Val Lys Lys Asp Leu Ile Ile Lys Leu Pro Lys Tyr Ser Leu
    1190                1195                1200
Phe Glu Leu Glu Asn Gly Arg Lys Arg Met Leu Ala Ser Ala Gly
    1205                1210                1215
Glu Leu Gln Lys Gly Asn Glu Leu Ala Leu Pro Ser Lys Tyr Val
    1220                1225                1230
Asn Phe Leu Tyr Leu Ala Ser His Tyr Glu Lys Leu Lys Gly Ser
    1235                1240                1245
Pro Glu Asp Asn Glu Gln Lys Gln Leu Phe Val Glu Gln His Lys
    1250                1255                1260
His Tyr Leu Asp Glu Ile Ile Glu Gln Ile Ser Glu Phe Ser Lys
    1265                1270                1275
Arg Val Ile Leu Ala Asp Ala Asn Leu Asp Lys Val Leu Ser Ala
    1280                1285                1290
Tyr Asn Lys His Arg Asp Lys Pro Ile Arg Glu Gln Ala Glu Asn
    1295                1300                1305
Ile Ile His Leu Phe Thr Leu Thr Asn Leu Gly Ala Pro Ala Ala
    1310                1315                1320
Phe Lys Tyr Phe Asp Thr Thr Ile Asp Arg Lys Arg Tyr Thr Ser
    1325                1330                1335
Thr Lys Glu Val Leu Asp Ala Thr Leu Ile His Gln Ser Ile Thr
    1340                1345                1350
```

Gly Leu Tyr Glu Thr Arg Ile Asp Leu Ser Gln Leu Gly Gly Asp
    1355                1360                1365

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Ser Gly
1

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Gly Ser Glu Thr Pro Gly Thr Ser Glu Ser Ala
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Gly Ser Glu Thr Pro Gly Thr Ser Glu Ser Ala Thr Pro Glu Ser
1               5                   10                  15

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ser Gly Ser Glu Thr Pro Gly Thr Ser Glu Ser Ala Thr Pro Glu Gly
1               5                   10                  15
Gly Ser Gly Gly Ser
            20

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gccgaggtga agttcgaggg cgac                                          24

<210> SEQ ID NO 27
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
cctacggcgt gcagtgcttc agc                                              23

<210> SEQ ID NO 28
<211> LENGTH: 332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
acgtaaacgg ccacaagttc agcgtgtccg gcgagggcga gggcgatgcc acctacggca      60
agctgaccct gaagttcatc tgcaccaccg gcaagctgcc cgtgccctgg cccaccctcg     120
tgaccaccct gacctacggc gtgcagtgct tcagccgcta ccccgaccac atgaagcagc     180
acgacttctt caagtccgcc atgcccgaag gctacgtcca ggagcgcacc atcttcttca     240
aggacgacgg caactacaag acccgcgccg aggtgaagtt cgagggcgac accctggtga     300
accgcatcga gctgaagggc atcgacttca ag                                    332

<210> SEQ ID NO 29
<211> LENGTH: 295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gtccggcgag ggcgagggcg atgccaccta cggcaagctg accctgaagt tcatctgcac      60
caccggcaag ctgcccgtgc cctggcccac cctcgtgacc accctgacct acggcgtgca     120
gtgcttcagc cgctaccccg accacatgaa gcagcacgac ttcttcaagt ccgccatgcc     180
cgaaggctac gtccaggagc gcaccatctt cttcaaggac gacggcaact acaagacccg     240
cgtcgagggc gacaccctgg tgaaccgcat cgagctgaag ggcatcgact tcaag          295

<210> SEQ ID NO 30
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
tccggcgagg gcgagggcga tgccacctac ggcaagctga ccctgaagtt catctgcacc      60
accggcaagc tgcccgtgcc ctggcccacc ctcgtgacca ccctgacgag ggcgacaccc     120
tggtgaaccg catcgagctg aagggcatcg acttcaag                              158

<210> SEQ ID NO 31
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 31

```
tccggcgagg gcgagggcga tgccacctac ggcaagctga ccctgaagtt catctgcacc      60
accggcaagc tgcccgtgcc ctggcccacc ctcgtgaaca ccctgaccta cgtgcagtgc     120
ttcagccgct accccgacca catgaagcag cacgacttct tcaagtccgc catgcccgaa     180
ggctacgtcc aggagcgcac catcttcttc aaggacgacg gcaactacaa gttcgagggc     240
gacaccctgg tgaaccgcat cgagctgaag ggcatcgact tcaag                     285
```

<210> SEQ ID NO 32
<211> LENGTH: 301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ccggcgaggg cgagggcgat gccacctacg gcaagctgac cctgaagttc atctgcacca      60
ccggcaagct gcccgtgccc tggcccaccc tcgtgaccac cctgacctac gtgcagtgct     120
tcagccgcta ccccgaccac atgaagcagc acgacttctt caagtccgcc atgcccgaag     180
gctacgtcca ggagcgcacc atcttcttca aggacgacgg caactacaag acccgcgccg     240
aggtgaagtt cgagggcgac accctggtga accgcatcga gctgaagggc atcgacttca     300
a                                                                     301
```

<210> SEQ ID NO 33
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

```
tccggcgagg gcgagggcga tgccacctac ggcaagctga ccctgaagtt catctgcacc      60
accggcaagc tgcccgtgcc ctggcccacc ctcgtgacca ccctgaccta cggacaccct     120
ggtgaaccgc atcgagctga agggcatcga cttcaa                               156
```

<210> SEQ ID NO 34
<211> LENGTH: 197
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
gtaaacggcc acaagttcag cgtgcagtgc ttcagccgct accccgacca catgaagcag      60
cacgacttct tcaagtccgc catgcccgaa ggctacgtcc aggagcgcac catcttcttc     120
aaggacgacg gcaactacaa gacggcaact acaagttcga gggcgacacc ctggtgaacc     180
gcatcgagct gaagggc                                                   197
```

<210> SEQ ID NO 35
<211> LENGTH: 283
<212> TYPE: DNA
<213> ORGANISM: Artificial Sequence
<220> FEATURE:
<223> OTHER INFORMATION: Description of Artificial Sequence: Synthetic

```
                        polynucleotide

<400> SEQUENCE: 35
ccacaagttc agcgtgtccg gcgagggcga gggcgatgcc acctacggca agctgaccct    60
gaagttcatc tgcaccaccg gcaagctgcc cgtgccctgg cccacccctcg tgaccaccct  120 gacctacggc gtgcagtgct tcagccgcta ccccgaccac atgaagcagc acgacttctt  180
caagtccgcc atgcccgaag ctacgtccag gagcgcacc atcttcttca aggacgacgg   240
caactacaag acaccgcatc gagctgaagg gcatcgactt caa                    283

<210> SEQ ID NO 36
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
ggccacaagt tcagcgtgtc cggcgagggc gagggcgatg ccacctacgg caagctgacc    60
ctgaagttca tctgcaccac cggcaccatc aaggacgacg gcaactacaa gacccgcgcc  120
gaagttcgag ggcgacaccc tggtgaaccg catcgagctg aagggcatcg acttc        175

<210> SEQ ID NO 37
<211> LENGTH: 291
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 37
taaacggcca caagttcagc gtgtccggcg agggcgaggg cgatgccacc tacggcaagc    60
tgaccctgaa gttcatctgc accaccggca agctgcccgt gccctggccc accctcgtga  120 ccacccctgac ctacggcgtg cagtgcttca gccgctaccc cgaccacatg aagcagcacg  180
acttcttcaa gtccgccatg cccgaaggct acgtccagga gcgcaccatc ttcttcaagg  240
acgacggcaa ctacaagacc tggtgaaccg catcgagctg aagggcatcg a            291

<210> SEQ ID NO 38
<211> LENGTH: 314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38
cacaagttca gcgtgtccgg cgagggcgag ggcgatgcca cctacggcaa gctgaccctg    60
aagttcatct gcaccaccgg caagctgccc gtgccctggc ccaccctcgt gaccaccctg  120
acctacggcg tgcagtgctt cagccgctac cccgaccaca tgaagcagca cgacttcttc  180
aagtccgcca tgcccgaagg ctacgtccag gagcgcacca tcttcttcaa ggacgacggc  240
aactacaaga cccgcgccga ggttcgaggg cgacaccctg gtgaaccgca tcgagctgaa  300
gggcatcgac ttca                                                    314

<210> SEQ ID NO 39
<211> LENGTH: 316
<212> TYPE: DNA
```

<213> ORGANISM: Artificial Sequence
<220> FEATURE:
<223> OTHER INFORMATION: Description of Artificial Sequence: Synthetic
      polynucleotide

<400> SEQUENCE: 39

```
taaacggcca caagttcagc gtgtccggcg agggcgaggg cgatgccacc tacggcaagc    60
tgaccctgaa gttcatctgc accaccggca agctgcccgt gccctggccc accctcgtga   120
ccaccctgac ctacggcgtg cagtgcttca gccgctaccc cgaccacatg aagcagcacg   180
acttcttcaa gtccgccatg cccgaaggct acgtccagga gcgcaccatc ttcttcaagg   240
acgacggcaa ctacaagacc cgcgccgagg cgacaccct ggtgaaccgc atcgagctga   300
agggcatcga cttcaa                                                    316
```

<210> SEQ ID NO 40
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 40

```
aaacggccac aagttcagcg tgtccggcga gggcgagggc gatgccacct acggcaagct    60
gaccctgaag ttcatctgca ccaccggcaa gctgcccgtg ccctggccca ccctcgtgac   120
caccctgacc tacgtgcagt gcttcagccg ctaccccgac cacatgaagc agcacgactt   180
cttcaagtcc gccatgcccg aaggctacgt ccaggacgc accatcttct tcaaggacga   240
cggcaactac aagacccgcg ccgaggtgaa gttcgagggc gacaccctgg tgaaccgcat   300
cgagctgaag ggcatcga                                                  318
```

<210> SEQ ID NO 41
<211> LENGTH: 185
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41

```
acggccacaa gttcagcgtg tccggcgagg gcgagggcga tgccacctac ggcaagctga    60
ccctgaagtt catctgcacc accggcaagc tgcccgtgcc ctggcccacc ctcgtgacca   120
ccctgaccta cgtgaagttc gagggcgaca ccctggtgaa ccgcatcgag ctgaagggca   180
tcgac                                                                185
```

<210> SEQ ID NO 42
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42

```
aaacggccac aagttcagcg tgtccggcga gggcgagggc gatgccacct acggcaagct    60
gaccctgaag ttcatctgca ccaccggcaa gctgcccgtg ccctggccca ccctcgtgac   120
caccctgacc tacgtgaagt tcgagggcga caccctggtg aaccgcatcg agctgaaggg   180
```

```
<210> SEQ ID NO 43
<211> LENGTH: 242
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (132)..(132)
<223> OTHER INFORMATION: a, c, t, g, unknown or other
<220> FEATURE:
<221> NAME/KEY: modified_base
<222> LOCATION: (153)..(153)
<223> OTHER INFORMATION: a, c, t, g, unknown or other
<220> FEATURE:
<221> NAME/KEY: modified_base
<222> LOCATION: (174)..(174)
<223> OTHER INFORMATION: a, c, t, g, unknown or other

<400> SEQUENCE: 43
aaacggccac aagttcagcg tgtccggcga gggcgagggc gatgccacct acggcaagct      60
gaccctgaag ttcatctgca ccaccggcaa gctgcccgtg ccctggccca cccttccgcc     120
atgcccgaag gntacgtcca ggagcgcacc atnttcttca aggacgacgg caantacaag     180
acccgcgccg aagttcgagg cgacaccct ggtgaaccgc atcgagctga agggcatcga     240
ct                                                                   242

<210> SEQ ID NO 44
<211> LENGTH: 175
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
caccctgacc tacggcgtgc agtgcttcag ccgctacccc gaccacatga agcagcacga      60
cttcttcaag tccgccatgc ccgaaggcta cgtccaggag cgcaccatct tcttcaagga     120
cgacggcaac tacaagaccc gcgccgaggt gaagttcgag ggcgacaccc tggtg          175

<210> SEQ ID NO 45
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
caccctgacc tacgtgaagt tcgagggcga caccctggt                             39

<210> SEQ ID NO 46
<211> LENGTH: 161
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
caccctgacc tacggcgtgc agtgcttcag ccgctacccc gaccacatga agcagcacga      60
cttcttcaag tccgccatgc ccgaaggcta cgtccaggag cgcaccatct tcttcaagga     120
cgacggcaac tacaagaccc gcgccgaggg cgacaccctg g                         161
```

<210> SEQ ID NO 47
<211> LENGTH: 145
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
caccctgacc tcagccgcta ccccgaccac atgaagcagc acgacttctt caagtccgcc    60
atgcccgaag gctacgtcca ggagcgcacc atcttcttca aggacgacgg caactacaag   120
acccgcgccg aggcgacacc ctggt                                         145

<210> SEQ ID NO 48
<211> LENGTH: 153
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48
ttattataca tcggagccct gccaaaaaat caatgtgaag caaatcgcag cccgcctcct    60
gcctccgctc tactcactgg tgttcatctt tggttttgtg ggcaacatgc tggtcatcct   120
catcctgata aactgcaaaa ggctgaagag cat                                153

<210> SEQ ID NO 49
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
ttattataca tcggagccct gccaaaaaat caatgtgaag caaatcgcag cccgcctccg    60
ctctactcac tggtgttcat ctttggtttt gtgggcaaca tgctggtcat cct          113

<210> SEQ ID NO 50
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttattataca tcggagccct gccaaaaaat caatgtgaag caaatcgcag cccgcatgct    60
ggtcatcctc                                                          70

<210> SEQ ID NO 51
<211> LENGTH: 62
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base

```
<222> LOCATION: (1)..(20)
<223> OTHER INFORMATION: a, c, u or g and this region may encompass
      17-20 nucleotides wherein some positions may be absent

<400> SEQUENCE: 51
nnnnnnnnnn nnnnnnnnnn guuuuagagc uagaaauagc aaguuaaaau aaggcuaguc      60
cg                                                                    62

<210> SEQ ID NO 52
<211> LENGTH: 54
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u or g and this region may encompass
      17-20 nucleotides wherein some positions may be absent

<400> SEQUENCE: 52
nnnnnnnnnn nnnnnnnnnn guuuuagagc uagaaauagc aaguuaaaau aagg            54

<210> SEQ ID NO 53
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
guucacugcc guauaggcag cuaagaaa                                        28

<210> SEQ ID NO 54
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
guucacugcc guauaggcag                                                 20
```

MULTIPLEX GUIDE RNAS

CROSS-REFERENCE TO RELATED APPLICATIONS

This application is a 371 application of PCT/US2014/056416, filed Sep. 18, 2014, which claims the benefit of U.S. Provisional Patent Applications 61/921,007, filed on Dec. 26, 2013 and 61/930,782, filed on Jan. 23, 2014; U.S. patent application Ser. No. 14/211,117, filed on Mar. 14, 2014; and International Application Nos. PCT/US2014/029068, filed on Mar. 14, 2014; PCT/US2014/028630, filed on Mar. 14, 2014; PCT/US2014/035162, filed on Apr. 23, 2014; and PCT/US2014/029304, filed on Mar. 14, 2014. All of the foregoing are incorporated herein by reference.

FEDERALLY SPONSORED RESEARCH OR DEVELOPMENT

This invention was made with Government support under Grant No. DPI GM105378 awarded by the National Institutes of Health. The Government has certain rights in the invention.

TECHNICAL FIELD

Described are methods and constructs for the multiplex expression of highly active CRISPR guide RNAs (gRNAs) from RNA Polymerase II and III promoters, optionally in mammalian cells.

BACKGROUND

The Cas9 nuclease forms the basis of a programmable RNA-guided clustered, regularly interspaced, short palindromic repeats (CRISPR)/CRISPR-associated (Cas) system (Wiedenheft et al., Nature 482, 331-338 (2012); Horvath et al., Science 327, 167-170 (2010); Terns et al., Curr Opin Microbiol 14, 321-327 (2011)) that can be used to create site-specific breaks in target DNA sequences in vitro, in mammalian cells, and in living model organisms such as zebrafish (Wang et al., Cell 153, 910-918 (2013); Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Gratz et al., Genetics 194 (4):1029-35 (2013)). A short ~100 nt guide RNA (gRNA) complexes with Cas9 and directs the nuclease to a specific target DNA site; targeting is mediated by a sequence of at least 17-20 nucleotides (nts) at the 5' end of the gRNA, which are designed to be complementary to and interact via simple base pair complementarity between the first 17-20 nucleotides of an engineered gRNA and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). gRNAs can also direct catalytically inactivated Cas9 proteins (known as dCas9, see Jinek et al., Science 337:816-821 (2012)) that are in turn fused to effector domains (e.g., a transcriptional activation domain) see, e.g., U.S. Ser. No. 61/799,647, filed on Mar. 15, 2013, and 61/838,148, filed on Jun. 21, 2013, both of which are incorporated herein by reference. These latter systems enable RNA-guided recruitment of heterologous effector domains to genomic loci of interest.

SUMMARY

The present invention is based, at least in part, on the discovery that Csy4, an endoribonuclease that recognizes a short RNA hairpin sequence, can be used to cleave out multiple functional gRNAs encoded on a single longer RNA transcript (produced from an RNA pol II or III promoter) in which the individual gRNAs are separated by Csy4 cleavage sites.

Thus in a first aspect the invention provides deoxyribonucleic acid (DNA) molecules comprising a plurality of sequences encoding guide RNAs (gRNAs), wherein each gRNA is flanked by at least one Csy4 cleavage sequence comprising or consisting of the sequence

```
                                        (SEQ ID NO: 1)
GTTCACTGCCGTATAGGCAG
or
                                        (SEQ ID NO: 2)
GTTCACTGCCGTATAGGCAGCTAAGAAA.
```

In some embodiments the DNA molecule is operably linked to a promoter sequence.

In some embodiments the DNA molecule includes two, three, or more gRNA sequences, each flanked by at least one Csy4 cleavage sequence.

In some embodiments, the promoter sequence is a RNA Polymerase II (Pol II) promoter or Pol III promoter, preferably a RNA Pol II promoter. In some embodiments the Pol II promoter is selected from the group consisting of CAG, EF1A, CAGGS, PGK, UbiC, CMV, B29, Desmin, Endoglin, FLT-1, GFPA, and SYN1 promoters.

In another aspect the invention provides a DNA molecule comprising a promoter sequence linked with one, two, three or more cassettes comprising: a sequence encoding a guide RNA, i.e., a sequence of about 100 nts, e.g., 95-300 nts, e.g., 95-105 nts for an *S. pyogenes*-based system, linked to a Csy4 cleavage site, e.g., SEQ ID NO:1 or 2.

In some embodiments the DNA molecule comprises a Pol II promoter, operably linked to a first sequence encoding a first guide RNA linked to a Csy4 cleavage site, linked to a second sequence encoding a second guide RNA linked to a Csy4 cleavage site, linked to a third sequence encoding a third guide RNA linked to a Csy4 cleavage site. In some embodiments, further guide RNAs linked to Csy4 cleavage sites are included. For example, the DNA molecule can have the following structure:

Promoter—C4—gRNA—C4—gRNA—C4—gRNA—C4

Promoter—C4—gRNA—C4—gRNA—C4—gRNA—C4—gRNA—C4

Promoter—C4—gRNA—C4—gRNA—C4—gRNA—C4—gRNA—C4—gRNA C4

And so on. In this illustration C4 is a sequence encoding a Csy4 RNA cleavage site and gRNA is a sequence encoding a guide RNA.

In some embodiments, the the Cas9 sgRNA comprises the sequence:

(SEQ ID NO: 4)
($X_{17-20}$) GUUUUAGAGCUAUGCUGUUUUG ($X_N$);

(SEQ ID NO: 5)
($X_{17-20}$) GUUUUAGAGCUA;

(SEQ ID NO: 6)
($X_{17-20}$) GUUUUAGAGCUAUGCUGUUUUG;

(SEQ ID NO: 7)
($X_{17-20}$) GUUUUAGAGCUAUGCU;

(SEQ ID NO: 8)
($X_{17-20}$) GUUUUAGAGCUAGAAAUAGCAAGUUAAAAUAAGGCUAGUCCG($X_N$);

(SEQ ID NO: 9)
($X_{17-20}$) GUUUUAGAGCUAUGCUGAAAAGCAUAGCAAGUUAAAAUAAGGCUAGUCCGUUAUC($X_N$);

(SEQ ID NO: 10)
($X_{17-20}$) GUUUUAGAGCUAUGCUGUUUUGGAAACAAAACAGCAUAGCAAGUUAAAAUAAGGCUAGUCCGUUAUC($X_N$);

(SEQ ID NO: 11)
($X_{17-20}$) GUUUUAGAGCUAGAAAUAGCAAGUUAAAAUAAGGCUAGUCCGUUAUCAACUUGAAAAAGUGGCACCGAGUCGGUGC($X_N$), (SEQ ID NO: 12)
($X_{17-20}$) GUUUAAGAGCUAGAAAUAGCAAGUUUAAAUAAGGCUAGUCCGUUAUCAACUUGAAAAAGUGGCACCGAGUCGGUGC;

(SEQ ID NO: 13)
($X_{17-20}$) GUUUUAGAGCUAUGCUGGAAACAGCAUAGCAAGUUUAAAUAAGGCUAGUCCGUUAUCAACUUGAAAAAGUGGCACCGAGUCGGUGC; or (SEQ ID NO: 14)
($X_{17-20}$) GUUUAAGAGCUAUGCUGGAAACAGCAUAGCAAGUUUAAAUAAGGCUAGUCCGUUAUCAACUUGAAAAAGUGGCACCGAGUCGGUGC, wherein $X_{17-20}$ is a sequence complementary to the complementary strand of 17-20 consecutive nucleotides of a target sequence, preferably a target sequence immediately 5' of a protospacer adjacent motif (PAM), and $X_N$ is any sequence that does not interfere with the binding of the ribonucleic acid to Cas9. Although a sequence of $X_{17-20}$ is exemplified herein with the S. pyogenes Cas9 system, longer sequences can also be used, e.g., as appropriate for other systems.

In some embodiments, the DNA molecule also includes a sequence encoding a functional Csy4 enzyme.

Also provided herein are vectors comprising the DNA molecules described herein, e.g., optionally comprising a sequence encoding a functional Csy4 enzyme. Also provided herein are the multiplex transcripts produced by the DNA molecules, e.g., intact RNAs that have not yet been cleaved with Csy4.

In yet another aspect, provided herein are methods for producing a plurality of guide RNAs in a cell. The methods include expressing the DNA molecules described herein in the cell.

In some embodiments, the cell is a mammalian cell, and the cell also expresses an exogenous functional Csy4 enzyme sequence, or the method further comprises administering a functional Csy4 enzyme or nucleic acid encoding a functional Csy4 enzyme.

In another aspect the invention provides methods for altering expression of one or a plurality of target genes in a cell. The methods include expressing a DNA molecule as described herein, e.g., a DNA molecule comprising a plurality of sequences encoding guide RNAs (gRNAs), wherein each gRNA comprises a variable sequence that is complementary to at least 17-20 nts of the one or more target genes, and each gRNA is flanked by at least one Csy4 cleavage sequence comprising or consisting of the sequence (SEQ ID NO: 1)
GTTCACTGCCGTATAGGCAG
or (SEQ ID NO: 2)
GTTCACTGCCGTATAGGCAGCTAAGAAA.

In the present methods and compositions, the gRNA can be either a single guide RNA comprising a fused tracrRNA and crRNA, as described herein, or can include just a crRNA, and the tracrRNA can be expressed from the same or a different DNA molecule. Thus in some embodiments the DNA molecules described herein also include a sequence encoding a tracrRNA. In some embodiments, the methods include expressing in the cells a separate tracrRNA, e.g., contacting the cells with a vector or DNA molecule that expresses a tracrRNA.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 5A-C are sequences showing evidence of 2-target multiplex editing in single human cells. Individual deletions are observed at intended site 2 or 3. Multiple deletions on the same sequence are observed for sites 2 and 3. Deletions spanning sites 2 and 3 are also observed.

FIG. 6 is a schematic showing successful multiplex expression of three gRNAs using the Csy4-based system.

DETAILED DESCRIPTION

Figure 1:
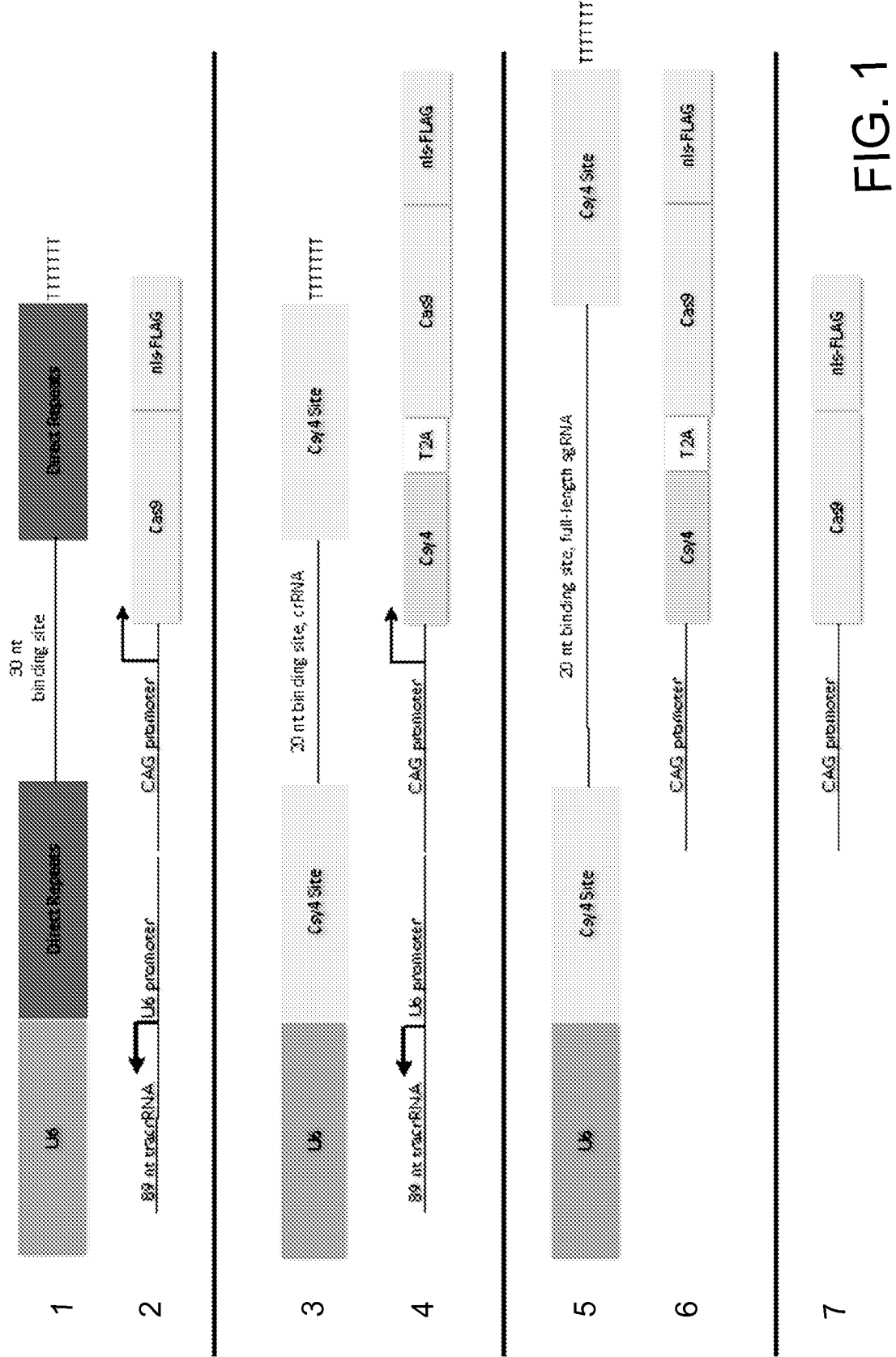
FIG. 1 is a schematic illustrating constructs used in initial multiplex experiments, as follows:
1+2: direct repeat crRNA array and Cas9, with separate tracrRNA
3+4: short crRNA array separated by Csy4 sites with Csy4, Cas9, and separate tracrRNA
5+6: full-length chimeric gRNAs separated by Csy4 site.
7: nls-FLAG tagged Cas9

One potential advantage of the Cas9 system is the capability to recruit either nuclease activity or heterologous effector domains to more than one genomic locus or target site in a cell. However, such multiplex applications require the ability to efficiently express more than one gRNA in a cell. For mammalian cells, RNA polymerase III promoters (e.g., U6 promoter) have been used to express single short gRNAs. Previous attempts to express multiple gRNA components in human cells from a single transcript have not proven to be efficient.

Additional desirable capabilities for the Cas9 system would be to create inducible versions of the components and to enable tissue-specific expression of the components. RNA polymerase II promoters that are inducible and/or tissue-specific have been previously described. However, although Cas9 or dCas9 proteins could be expressed from such RNA pol II promoters, short, defined gRNAs cannot be expressed in this way as the start and stop sites of transcription from RNA pol II are imprecise. Indeed, to date, all gRNAs have been expressed from RNA polymerase III promoters, which are ideally suited for expression of short RNAs.

As demonstrated herein, Csy4, an endoribonuclease that recognizes a short RNA hairpin sequence, can be used to cleave out multiple functional gRNAs encoded on a single longer RNA transcript (produced from an RNA pol III promoter) cassette in which the individual gRNAs are separated by Csy4 cleavage sites. Functional gRNAs can be successfully cleaved from longer RNA transcripts expressed from an RNA pol II promoter.

gRNA/Csy4 Multimeric Cassettes

Thus described herein are DNA molecules that encode longer RNA transcripts, referred to herein as multimeric cassettes, which include two or more gRNA sequences, wherein each gRNA is flanked by a Csy4 cleavage sequence. The DNA molecules can also include a promoter, and can optionally include one or more other transcription regulatory sequences, e.g., enhancers, silencers, insulators, and polyA sequences. See, e.g., Xu et al., Gene. 2001 Jul. 11; 272(1-2):149-56.

Promoters

A number of promoters are known in the art that can be used in the present methods. In some embodiments, the promoter is a PolII or Pol III promoter, preferably a Pol II promoter. Various Pol II promoters have been described and can be used in the present compositions and methods, including the CAG promoter (see, e.g., Alexopoulou et al., BMC Cell Biology 9: 2, 2008; Miyazaki et al., Gene 79 (2): 269-77 (1989); Niwa et al., Gene 108 (2): 193-9 (1991); additional promoters include the EF1A, CAGGS, PGK, UbiC and CMV promoters, as well as tissue-specific promoters such as B29, Desmin, Endoglin, FLT-1, GFPA, SYN1, among others; sequences of numerous promoters are known in the art. For example, the CMV and PGK promoters can be amplified from pSicoR and pSicoR PGK respectively (Ventura et al., Proc Natl Acad Sci USA 101: 10380-10385 (2004)), the UbiC promoter can be amplified from pDSL_hpUGIH (ATCC), the CAGGS promoter can be amplified from pCAGGS (BCCM), and the EF1A promoter can be amplified from the pEF6 vector (Invitrogen). The Pol II core promoter is described in Butler and Kadonaga, Genes & Dev. 16: 2583-2592 (2002). Cleavage of the gRNAs out of a larger transcript driven by Pol II expression enables one to produce gRNAs that have any nucleotide at the 5'-most position (standard expression from a U6 or other RNA polymerase III promoter places restrictions on the identity of this nucleotide).

In some embodiments, a tissue-specific promoter is used, and a short, defined gRNA sequence can be processed out of the RNA-Pol II transcript.

A number of Pol III promoters are known in the art, including the U6 small nuclear (sn) RNA promoter, 7SK promoter, and the H1 promoter. See, e.g., Ro et al., BioTechniques, 38(4):625-627 (2005).

Guide RNAs

Cas9 nuclease can be guided to specific genomic targets of at least 17-20 nts bearing an additional proximal protospacer adjacent motif (PAM) of sequence NGG by using a single gRNA bearing at least 17-20 nts at its 5' end that are complementary to the genomic DNA target site.

Thus, the compositions described herein can include a sequence encoding a single guide RNA (sgRNA) comprising a crRNA fused to a normally trans-encoded tracrRNA, e.g., a single Cas9 guide RNA as described in Mali et al., Science 2013 Feb. 15; 339(6121):823-6, with a sequence at the 5' end that is complementary to 17-20 nucleotides (nts) of a target sequence immediately 5' of a protospacer adjacent motif (PAM), e.g., NGG, NAG, or NNGG.

Methods of designing and expressing guide RNAs are known in the art. Guide RNAs generally speaking come in two different systems: 1) System 1 uses separate crRNA and tracrRNAs that function together to guide cleavage by Cas9; and 2) System 2 uses a chimeric crRNA-tracrRNA hybrid that combines the two separate guide RNAs in a single system (Jinek et al. 2012). The tracr-RNA can be variably truncated and a range of lengths has been shown to function in both the separate system (system 1) and the chimeric gRNA system (system 2). See, e.g., Jinek et al., Science 2012; 337:816-821; Mali et al., Science. 2013 Feb. 15; 339(6121):823-6; Cong et al., Science. 2013 Feb. 15; 339 (6121):819-23; and Hwang and Fu et al., Nat Biotechnol. 2013 March; 31(3):227-9; Jinek et al., Elife 2, e00471 (2013)). For System 2, generally the longer length chimeric gRNAs have shown greater on-target activity but the relative specificities of the various length gRNAs currently remain undefined and therefore it may be desirable in certain instances to use shorter gRNAs. In some embodiments, the gRNAs are complementary to a region that is within about 100-800 bp upstream of the transcription start site, e.g., is within about 500 bp upstream of the transcription start site, includes the transcription start site, or within about 100-800 bp, e.g., within about 500 bp, downstream of the transcription start site. In some embodiments, vectors (e.g., plasmids) encoding more than one gRNA are used, e.g., plasmids encoding, 2, 3, 4, 5, or more gRNAs directed to different sites in the same region of the target gene. Additional guide RNAs, and methods of increasing the specificity of genome editing, are described in Provisional Patent Application Ser. No. 61/838,178, entitled INCREASING SPECIFICITY FOR RNA-GUIDED GENOME EDITING.

In some embodiments, the gRNA comprises or consists of the sequence:

(SEQ ID NO: 4)
($X_{17-20}$) GUUUUAGAGCUAUGCUGUUUUG ($X_N$);

(SEQ ID NO: 5)
($X_{17-20}$) GUUUUAGAGCUA;

(SEQ ID NO: 6)
($X_{17-20}$) GUUUUAGAGCUAUGCUGUUUUG;

(SEQ ID NO: 7)
($X_{17-20}$) GUUUUAGAGCUAUGCU;

(SEQ ID NO: 8)
($X_{17-20}$) GUUUUAGAGCUAGAAAUAGCAAGUUAAAAUAAGGCUAGUCCG ($X_N$);

(SEQ ID NO: 9)
($X_{17-20}$) GUUUUAGAGCUAUGCUGAAAAGCAUAGCAAGUUAAAAUAAGGCUAGUCCGUUAUC ($X_N$);

(SEQ ID NO: 10)
($X_{17-20}$) GUUUUAGAGCUAUGCUGUUUUGGAAACAAAACAGCAUAGCAAGUUAAAAUAAGGCUAGUCCGUUAUC ($X_N$);

(SEQ ID NO: 11)
($X_{17-20}$) GUUUUAGAGCUAGAAAUAGCAAGUUAAAAUAAGGCUAGUCCGUUAUCAACUUGAAAAAGUGGCACCGAGUCGGUGC ($X_N$), (SEQ ID NO: 12)
($X_{17-20}$) GUUUAAGAGCUAGAAAUAGCAAGUUUAAAUAAGGCUAGUCCGUUAUCAACUUGAAAAAGUGGCACCGAGUCGGUGC;

(SEQ ID NO: 13)
($X_{17-20}$) GUUUUAGAGCUAUGCUGGAAACAGCAUAGCAAGUUUAAAUAAGGCUAGUCCGUUAUCAACUUGAAAAAGUGGCACCGAGUCGGUGC;
or (SEQ ID NO: 14)
($X_{17-20}$) GUUUAAGAGCUAUGCUGGAAACAGCAUAGCAAGUUUAAAUAAGGCUAGUCCGUUAUCAACUUGAAAAAGUGGCACCGAGUCGGUGC, wherein $X_{17-20}$ is a sequence complementary to the complementary strand of at least 17-20 consecutive nucleotides of a target sequence (though in some embodiments this complementarity region may be longer than 20 nts, e.g., 21, 22, 23, 24, 25, 26, 27, 28, 29, or 30 or more nts, e.g., 17-30 nts), preferably a target sequence immediately 5' of a protospacer adjacent motif (PAM), e.g., NGG, NAG, or NNGG. $X_N$ is any sequence, wherein N (in the RNA) can be 0-300 or 0-200, e.g., 0-100, 0-50, or 0-20, that does not interfere with the binding of the ribonucleic acid to Cas9. In some embodiments the RNA includes one or more U, e.g., 1 to 8 or more Us (e.g., U, UU, UUU, UUUU, UUUUU, UUUUUU, UUUUUUU, UUUUUUUU) at the 3' end of the molecule, as a result of the optional presence of one or more Ts used as a termination signal to terminate RNA PolIII transcription. In some embodiments the RNA includes one or more, e.g., up to 3, e.g., one, two, or three, or more additional nucleotides at the 5' end of the RNA molecule that is not complementary to the target sequence. Optionally, one or more of the RNA nucleotides is modified, e.g., locked (2'-O-4'-C methylene bridge), is 5'-methylcytidine, is 2'-O-methyl-pseudouridine, or in which the ribose phosphate backbone has been replaced by a polyamide chain, e.g., one or more of the nucleotides within the sequence $X_{17-20}$, one or more of the nucleotides within the sequence $X_N$, or one or more of the nucleotides within any sequence of the gRNA For example, in some embodiments the chimeric guide RNAs described in Jinek et al. (Science. 337(6096):816-21 (2012)) can be used, e.g., (SEQ ID NO: 8)
($X_{17-20}$) GUUUUAGAGCUAGAAAUAGCAAGUUAAAAUAAGGCUAGUCCG;

(SEQ ID NO: 9)
($X_{17-20}$) GUUUUAGAGCUAGAAAUAGCAAGUUAAAAUAAGG;

in some embodiments, the sgRNA bearing a 5'-terminal 17-20-nucleotide sequence complementary to the target DNA sequence, and a 42-nucleotide 3'-terminal stem loop structure required for Cas9 binding described in Jinek et al., Elife. 2:e00471 (2013), e.g., ($X_{17-20}$) GUUUUAGAGCUAGAAAUAGCAAGUUAAAAUAAGGCUAGUCCG (SEQ ID NO:8) are used.

In some embodiments, the guide RNA includes one or more Adenine (A) or Uracil (U) nucleotides on the 3' end.

Although the examples described herein utilize a single gRNA, the methods can also be used with dual gRNAs (e.g., the crRNA and tracrRNA found in naturally occurring systems). In this case, a single tracrRNA would be used in conjunction with multiple different crRNAs expressed using the present system, e.g., the following (note that for RNAs, T's are understood herein to be U's):

crRNA sequence: $X_{17-20}$-GTTTTAGAGCTAGAAA (SEQ ID NO:15)

tracrRNA sequence: TAGCAAGT-TAAAATAAGGCTAGTCCGTTATCAACTT-GAAAAAGTGGCACCGAGT CGGTGC (SEQ ID NO:16). In this case, the crRNA is used as the guide RNA in the methods and molecules described herein, and the tracrRNA can be expressed from the same or a different DNA molecule.

Furthermore, although guide RNAs having a sequence of 17-20 nucleotides of complementarity are exemplified herein, in some embodiments longer sequences can be used, e.g., 21, 22, 23, 24, 25, 26, 27, 28, 29, or 30 or more nts, e.g., 17-30 nts in place of 17-20 nts.

Csy4 Cleavage Sequences

In the methods and compositions described herein, a Csy4 cleavage sequence is inserted into the DNA molecule such that each guide RNA is flanked by a cleavage sequence, with one or at least one cleavage sequence between each guide RNA. Exemplary Csy4 cleavage sequences include GTTCACTGCCGTATAGGCAG (truncated 20 nt) (SEQ ID NO:1) and GTTCACTGCCGTATAGGCAGCTAAGAAA (full 28 nt) (SEQ ID NO:2). As demonstrated herein, use of the truncated Csy4 cleavage site (SEQ ID NO:1) is more efficient in human cells than use of the standard site. To the best of the present inventors' knowledge, this is the first demonstration of Csy4 activity being utilized in human cells.

Functional Csy4 Enzyme Sequences

In the methods described herein, a functional Csy4 enzyme that is capable of cleaving the transcripts at the Csy4 cleavage sites, is also expressed in the cell.

Exemplary Csy4 sequences from Csy4 homologues from *Pseudomonas aeruginosa* UCBPP-PA14 (Pa14), *Yersinia pestis* AAM85295 (Yp), *Escherichia coli* UTI89 (Ec89), *Dichelobacter nodosus* VCS1703A (Dn), *Acinetobacter baumannii* AB0057 (Ab), *Moritella* sp. PE36 (MP1, MP01),

*Shewanella* sp. W3-18-1 (SW), *Pasteurella multocida* subsp. *multocida* Pm70 (Pm), *Pectobacterium wasabiae* (Pw), and *Dickeya dadantii* Ech703 (Dd) are set forth in Fig. S6 of Haurwitz et al., Science 329(5997): 1355-1358 (2010). In preferred embodiments, the Csy4 is from *Pseudomonas aeruginosa*.

In some embodiments, the Csy4 is also used to covalently link heterologous effector domains to the gRNAs. Csy4 is believed to be a single-turnover enzyme and remains bound to its target hairpin sequence after cleavage (Sternberg et al., RNA. 2012 April; 18(4):661-72). Csy4 is thus expected to remain bound to the 3' end of each cleaved gRNA. Since as demonstrated herein the cleaved gRNAs appear to be functional in human cells, the presence of this Csy4 protein on the 3' end of the gRNA does not appear to affect the ability of the gRNA to complex with and direct Cas9 activity. Thus it is presumed that these gRNA-Csy4 fusions would also be able to direct Cas9 mutants that bear mutations that inactivate its catalytic nuclease activity (dCas9 proteins). Therefore, one could fuse heterologous functional domains (HFD) to Csy4 (Csy4-HFD), and a dCas9:sgRNA:Csy4-HFD complex could then direct such domains to a specific genomic locus. Examples of such HFD could include other nuclease domains such as that from FokI, transcriptional activator or repressor domains, or other domains that modify histones or DNA methylation status.

The Csy4-HFD are created by fusing a heterologous functional domain (e.g., a transcriptional activation domain, e.g., from VP64 or NF-κB p65), to the N-terminus or C-terminus of a Csy4 protein, with or without an intervening linker, e.g., a linker of about 5-20 or 13-18 nucleotides. The transcriptional activation domains can be fused on the N or C terminus of the Csy4. In addition to transcriptional activation domains, other heterologous functional domains (e.g., transcriptional repressors (e.g., KRAB, SID, and others) or silencers such as Heterochromatin Protein 1 (HP1, also known as swi6), e.g., HP1α or HP1β; proteins or peptides that could recruit long non-coding RNAs (lncRNAs) fused to a fixed RNA binding sequence such as those bound by the MS2 coat protein, endoribonuclease Csy4, or the lambda N protein; enzymes that modify the methylation state of DNA (e.g., DNA methyltransferase (DNMT) or TET proteins); or enzymes that modify histone subunits (e.g., histone acetyltransferases (HAT), histone deacetylases (HDAC), histone methyltransferases (e.g., for methylation of lysine or arginine residues) or histone demethylases (e.g., for demethylation of lysine or arginine residues)) as are known in the art can also be used. A number of sequences for such domains are known in the art, e.g., a domain that catalyzes hydroxylation of methylated cytosines in DNA. Exemplary proteins include the Ten-Eleven-Translocation (TET)1-3 family, enzymes that converts 5-methylcytosine (5-mC) to 5-hydroxymethylcytosine (5-hmC) in DNA. See, e.g., WO/2014/144761.

Sequences for human TET1-3 are known in the art and are shown in the following table:

| | GenBank Accession Nos. | |
| --- | --- | --- |
| Gene | Amino Acid | Nucleic Acid |
| TET1 | NP_085128.2 | NM_030625.2 |
| TET2* | NP_001120680.1 (var 1) | NM_001127208.2 |
| | NP_060098.3 (var 2) | NM_017628.4 |
| TET3 | NP_659430.1 | NM_144993.1 |

*Variant (1) represents the longer transcript and encodes the longer isoform (a). Variant (2) differs in the 5' UTR and in the 3' UTR and coding sequence compared to variant 1. The resulting isoform (b) is shorter and has a distinct C-terminus compared to isoform a.

In some embodiments, all or part of the full-length sequence of the catalytic domain can be included, e.g., a catalytic module comprising the cysteine-rich extension and the 2OGFeDO domain encoded by 7 highly conserved exons, e.g., the Tet1 catalytic domain comprising amino acids 1580-2052, Tet2 comprising amino acids 1290-1905 and Tet3 comprising amino acids 966-1678. See, e.g., FIG. 1 of Iyer et al., Cell Cycle. 2009 Jun. 1; 8(11):1698-710. Epub 2009 Jun. 27, for an alignment illustrating the key catalytic residues in all three Tet proteins, and the supplementary materials thereof (available at ftp site ftp.ncbi.nih-.gov/pub/aravind/DONS/supplementary_material_DON-S.html) for full length sequences (see, e.g., seq 2c); in some embodiments, the sequence includes amino acids 1418-2136 of Tet1 or the corresponding region in Tet2/3.

Other catalytic modules can be, e.g., from the proteins identified in Iyer et al., 2009.

In some embodiments, the fusion proteins include a linker between the Csy4 and the heterologous functional domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:3) or GGGGS (SEQ ID NO:17), e.g., two, three, four, or more repeats of the GGGS (SEQ ID NO:3) or GGGGS (SEQ ID NO:17) unit. Other linker sequences can also be used, e.g., GGS, GGSG (SEQ ID NO:22), SGSET-PGTSESA (SEQ ID NO:23), SGSETPGTSESATPES (SEQ ID NO:24), or SGSETPGTSESATPEGGSGGS (SEQ ID NO:25).

Cas9

In the methods described herein, Cas9 is also expressed in the cells. A number of bacteria express Cas9 protein variants. The Cas9 from *Streptococcus pyogenes* is presently the most commonly used; some of the other Cas9 proteins have high levels of sequence identity with the *S. pyogenes* Cas9 and use the same guide RNAs. Others are more diverse, use different gRNAs, and recognize different PAM sequences as well (the 2-5 nucleotide sequence specified by the protein which is adjacent to the sequence specified by the RNA). Chylinski et al. classified Cas9 proteins from a large group of bacteria (RNA Biology 10:5, 1-12; 2013), and a large number of Cas9 proteins are listed in supplementary FIG. 1 and supplementary table 1 thereof, which are incorporated by reference herein. The constructs and methods described herein can include the use of any of those Cas9 proteins, and their corresponding guide RNAs or other guide RNAs that are compatible. The Cas9 from *Streptococcus thermophilus* LMD-9 CRISPR1 system has also been shown to function in human cells in Cong et al (Science 339, 819 (2013)). Additionally, Jinek et al. showed in vitro that Cas9 orthologs from *S. thermophilus* and *L. innocua*, (but not from *N. meningitidis* or *C. jejuni*, which likely use a different guide RNA), can be guided by a dual *S. pyogenes* gRNA to cleave target plasmid DNA, albeit with slightly decreased efficiency.

In some embodiments, the present system utilizes the Cas9 protein from *S. pyogenes*, either as encoded in bacteria or codon-optimized for expression in mammalian cells. An exemplary sequence of *Streptococcus pyogenes* Cas9 (residues 1-1368) fused to an HA epitope (amino acid sequence DAYPYDVPDYASL (SEQ ID NO:18)) and a nuclear localization signal (amino acid sequence PKKKRKVEDPKK-KRKVD (SEQ ID NO:19)) is as follows:

(SEQ ID NO: 20)
MDKKYSIGLDIGTNSVGWAVITDEYKVPSKKFKVLGNTDRHSIKKNLIG
ALLFDSGETAEATRLKRTARRRYTRRKNRICYLQEIFSNEMAKVDDSFF
HRLEESFLVEEDKKHERHPIFGNIVDEVAYHEKYPTIYHLRKKLVDSTD
KADLRLIYLALAHMIKFRGHFLIEGDLNPDNSDVDKLFIQLVQTYNQLF
EENPINASGVDAKAILSARLSKSRRLENLIAQLPGEKKNGLFGNLIALS
LGLTPNFKSNFDLAEDAKLQLSKDTYDDDLDNLLAQIGDQYADLFLAAK
NLSDAILLSDILRVNTEITKAPLSASMIKRYDEHHQDLTLLKALVRQQL
PEKYKEIFFDQSKNGYAGYIDGGASQEEFYKFIKPILEKMDGTEELLVK
LNREDLLRKQRTFDNGSIPHQIHLGELHAILRRQEDFYPFLKDNREKIE
KILTFRIPYYVGPLARGNSRFAWMTRKSEETITPWNFEEVVDKGASAQS
FIERMTNFDKNLPNEKVLPKHSLLYEYFTVYNELTKVKYVIEGMRKPAF
LSGEQKKAIVDLLFKINRKVTVKQLKEDYFKKIECFDSVEISGVEDRFN
ASLGTYHDLLKIIKDKDFLDNEENEDILEDIVLTLTLFEDREMIEERLK
TYAHLFDDKVMKQLKRRRYTGWGRLSRKLINGIRDKQSGKTILDFLKSD
GFANRNFMQLIHDDSLTFKEDIQKAQVSGQGDSLHEHIANLAGSPAIKK
GILQTVKVVDELVKVMGRHKPENIVIEMARENQTTQKGQKNSRERMKRI
EEGIKELGSQILKEHPVENTQLQNEKLYLYYLQNGRDMYVDQELDINRL
SDYDVDHIVPQSFLKDDSIDNKVLTRSDKNRGKSDNVPSEEVVKKMKNY
WRQLLNAKLITQRKFDNLIKAERGGLSELDKAGFIKRQLVETRQIIKHV
AQILDSRMNIKYDENDKLIREVKVIILKSKLVSDFRKDFQFYKVREINN
YHHAHDAYLNAVVGTALIKKYPKLESEFVYGDYKVYDVRKMIAKSEQEI
GKATAKYFFYSNIMNFFKTEITLANGEIRKRPLIETNGETGEIVWDKGR
DFATVRKVLSMPQVNIVKKTEVQTGGFSKESILPKRNSDKLIARKKDWD
PKKYGGFDSPTVAYSVLVVAKVEKGKSKKLKSVKELLGITIMERSSFEK
NPIDFLEAKGYKEVKKDLIIKLPKYSLFELENGRKRMLASAGELQKGNE
LALPSKYVNFLYLASHYEKLKGSPEDNEQKQLFVEQHKHYLDEIIEQIS
EFSKRVILADANLDKVLSAYNKHRDKPIREQAENIIHLFTLINLGAPAA
FKYFDTTIDRKRYTSTKEVLDATLIHQSITGLYETRIDLSQLGGDAYPY
DVPDYASLGSGSPKKKRKVEDPKKKRKVD

See Jinek et al, 2013, supra.

In some embodiment, a Cas9 sequence is used that contains either of the D10A and H840A mutations to render the nuclease a nickase, or both the D10A and H840A mutations to render the nuclease portion of the protein catalytically inactive. The sequence of a catalytically inactive *S. pyogenes* Cas9 (dCas9) that can be used in the methods and compositions described herein is as follows; the mutations are in bold and underlined.

(SEQ ID NO: 21)

```
              10         20         30         40         50         60
         MDKKYSIGLA IGTNSVGWAV ITDEYKVPSK KFKVLGNTDR HSIKKNLIGA LLFDSGETAE
              70         80         90        100        110        120
         ATRLKRTARR RYTRRKNRIC YLQEIFSNEM AKVDDSFFHR LEESFLVEED KKHERHPIFG
             130        140        150        160        170        180
         NIVDEVAYHE KYPTIYHLRK KLVDSTDKAD LRLIYLALAH MIKFRGHFLI EGDLNPDNSD
             190        200        210        220        230        240
         VDKLFIQLVQ TYNQLFEENP INASGVDAKA ILSARLSKSR RLENLIAQLP GEKKNGLFGN
             250        260        270        280        290        300
         LIALSLGLTP NFKSNFDLAE DAKLQLSKDT YDDDLDNLLA QIGDQYADLF LAAKNLSDAI
             310        320        330        340        350        360
         LLSDILRVNT EITKAPLSAS MIKRYDEHHQ DLTLLKALVR QQLPEKYKEI FFDQSKNGYA
             370        380        390        400        410        420
         GYIDGGASQE EFYKFIKPIL EKMDGTEELL VKLNREDLLR KQRTFDNGSI PHQIHLGELH
             430        440        450        460        470        480
         AILRRQEDFY PFLKDNREKI EKILTFRIPY YVGPLARGNS RFAWMTRKSE ETITPWNFEE
             490        500        510        520        530        540
         VVDKGASAQS FIERMTNFDK NLPNEKVLPK HSLLYEYFTV YNELTKVKYV TEGMRKPAFL
             550        560        570        580        590        600
         SGEQKKAIVD LLFKTNRKVT VKQLKEDYFK KIECFDSVEI SGVEDRFNAS LGTYHDLLKI
             610        620        630        640        650        660
         IKDKDFLDNE ENEDILEDIV LTLTLFEDRE MIEERLKTYA HLFDDKVMKQ LKRRRYTGWG
             670        680        690        700        710        720
         RLSRKLINGI RDKQSGKTIL DFLKSDGFAN RNFMQLIHDD SLTFKEDIQK AQVSGQGDSL
             730        740        750        760        770        780
         HEHIANLAGS PAIKKGILQT VKVVDELVKV MGRHKPENIV IEMARENQTT QKGQKNSRER
             790        800        810        820        830        840
         MKRIEEGIKE LGSQILKEHP VENTQLQNEK LYLYYLQNGR DMYVDQELDI NRLSDYDVDA
```

```
                                       -continued
           850          860          870          880          890          900
    IVPQSFLKDD   SIDNKVLTRS   DKNRGKSDNV   PSEEVVKKMK   NYWRQLLNAK   LITQRKFDNL 910          920          930          940          950          960
    TKAERGGLSE   LDKAGFIKRQ   LVETRQITKH   VAQILDSRMN   TKYDENDKLI   REVKVITLKS 970          980          990         1000 1010 1020
    KLVSDFRKDF   QFYKVREINN   YHHAHDAYLN   AVVGTALIKK   YPKLESEFVY   GDYKVYDVRK 1030         1040         1050         1060         1070         1080
    MIAKSEQEIG   KATAKYFFYS   NIMNFFKTEI   TLANGEIRKR   PLIETNGETG   EIVWDKGRDF 1090         1100         1110         1120         1130         1140
    ATVRKVLSMP   QVNIVKKTEV   QTGGFSKESI   LPKRNSDKLI   ARKKDWDPKK   YGGFDSPTVA 1150         1160         1170         1180         1190         1200
    YSVLVVAKVE   KGKSKKLKSV   KELLGITIME   RSSFEKNPID   FLEAKGYKEV   KKDLIIKLPK 1210         1220         1230         1240         1250         1260
    YSLFELENGR   KRMLASAGEL   QKGNELALPS   KYVNFLYLAS   HYEKLKGSPE   DNEQKQLFVE 1270         1280         1290         1300         1310         1320
    QHKHYLDEII   EQISEFSKRV   ILADANLDKV   LSAYNKHRDK   PIREQAENII   HLFTLTNLGA 1330         1340         1350         1360
    PAAFKYFDTT   IDRKRYTSTK   EVLDATLIHQ   SITGLYETRI   DLSQLGGD
```

See, e.g., Mali et al., 2013, supra; and Jinek et al., 2012, supra. Alternatively, the Cas9 can be a dCas9-heterofunctional domain fusion (dCas9-HFD) as described in U.S. Provisional Patent Application entitled RNA-GUIDED TARGETING OF GENETIC AND EPIGENOMIC REGULATORY PROTEINS TO SPECIFIC GENOMIC LOCI, filed on Jun. 21, 2013 and assigned Ser. No. 61/838,148, and in PCT/US2014/027335.

The Cas9 can be expressed from an expression vector, as described herein, e.g., an extrachromosomal plasmid or viral vector comprising a sequence encoding Cas9, e.g., a Cas9 cDNA or gene; can be expressed from an exogenous Cas9 cDNA or gene that has integrated into the genome of the cell; an mRNA encoding Cas9; the actual Cas9 protein itself; or, in the case of non-mammalian cells, can be an exogenous Cas9.

Expression Systems

Nucleic acid molecules comprising expression vectors can be used, e.g., for in vivo or in vitro expression of the Csy4/guide RNA constructs described herein. Vectors for expressing multiple gRNAs (potentially in an inducible or tissue-/cell-type specific fashion) can be used for research and therapeutic applications.

In order to use the fusion proteins and multimeric guide RNA cassettes described herein, it may be desirable to express them from a nucleic acid that encodes them. This can be performed in a variety of ways. For example, a nucleic acid encoding a guide RNA cassette or Csy4 or Cas9 protein can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the fusion protein or for production of the fusion protein. The nucleic acid encoding the guide RNA or fusion protein can also be cloned into an expression vector, for administration to a plant cell, animal cell, preferably a mammalian cell or a human cell, fungal cell, bacterial cell, or protozoan cell.

To obtain expression, a sequence encoding a guide RNA or fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., E. coli, Bacillus sp., and Salmonella (Palva et al., 1983, Gene 22:229-235). Kits for such expression systems are commercially available. Eukaryotic expression systems for mammalian cells, yeast, and insect cells are well known in the art and are also commercially available.

A number of suitable vectors are known in the art, e.g., viral vectors including recombinant retroviruses, lentivirus, adenovirus, adeno-associated virus, and herpes simplex virus 1, adenovirus-derived vectors, or recombinant bacterial or eukaryotic plasmids. For example, the expression construct can include: a coding region; a promoter sequence, e.g., a promoter sequence that restricts expression to a selected cell type, a conditional promoter, or a strong general promoter; an enhancer sequence; untranslated regulatory sequences, e.g., a 5'untranslated region (UTR), a 3'UTR; a polyadenylation site; and/or an insulator sequence. Such sequences are known in the art, and the skilled artisan would be able to select suitable sequences. See, e.g., Current Protocols in Molecular Biology, Ausubel, F. M. et al. (eds.) Greene Publishing Associates, (1989), Sections 9.10-9.14 and other standard laboratory manuals. In some embodiments, expression can be restricted to a particular cell type, using a tissue-specific promoter as is known in the art.

As described above, the vectors for expressing the guide RNAs can include RNA Pol II or Pol III promoters to drive expression of the guide RNAs. These human promoters allow for expression of gRNAs in mammalian cells following plasmid transfection. Alternatively, a T7 promoter may be used, e.g., for in vitro transcription, and the RNA can be transcribed in vitro and purified. The promoter used to direct expression of the nucleic acid depends on the particular application. For example, a strong constitutive promoter is typically used for expression and purification of fusion proteins. In contrast, when the fusion protein is to be administered in vivo for gene regulation, either a constitutive or an inducible promoter can be used, depending on the particular use of the fusion protein. In addition, a preferred promoter for administration of the fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the fusion protein, e.g., expression in plants, animals, bacteria, fungus, protozoa, etc. Standard bacterial expression vectors include plasmids such as pBR322 based plasmids, pSKF, pET23D, and commercially available tag-fusion expression systems such as GST and LacZ. A preferred tag-fusion protein is the maltose binding protein (MBP). Such tag-fusion proteins can be used for purification of the engineered TALE repeat protein. Epitope tags can also be added to recombinant proteins to provide convenient methods of isolation, for monitoring expression, and for monitoring cellular and subcellular localization, e.g., c-myc or FLAG Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the fusion protein encoding sequence under the direction of the polyhedrin promoter or other strong baculovirus promoters.

The elements that are typically included in expression vectors also include a replicon that functions in E. coli, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

In some embodiments, the Cas9 or Csy4 protein includes a nuclear localization domain which provides for the protein to be translocated to the nucleus. Several nuclear localization sequences (NLS) are known, and any suitable NLS can be used. For example, many NLSs have a plurality of basic amino acids, referred to as a bipartite basic repeats (reviewed in Garcia-Bustos et al, 1991, Biochim. Biophys. Acta, 1071:83-101). An NLS containing bipartite basic repeats can be placed in any portion of chimeric protein and results in the chimeric protein being localized inside the nucleus. In preferred embodiments a nuclear localization domain is incorporated into the final fusion protein, as the ultimate functions of the fusion proteins described herein will typically require the proteins to be localized in the nucleus. However, it may not be necessary to add a separate nuclear localization domain in cases where the protein has intrinsic nuclear translocation function.

The present invention includes the vectors and cells comprising the vectors.

Libraries

Also provided herein are combinatorial libraries of gRNAs, e.g., in inducible, tissue- or cell-type specific multiplex vectors for research applications, e.g., for screening for potential drug targets or to define interactions at a genetic level.

Methods of Use

The methods described can include expressing in a cell, or contacting the cell with, the multimeric cassettes as described herein, plus a nuclease that can be guided by the shortened gRNAs, e.g., a Cas9 nuclease as described above, and a Csy4 nuclease, as described above.

The described system is a useful and versatile tool for modifying the expression of multiple endogenous genes simultaneously, or for targeting multiple parts of a single gene. Current methods for achieving this require the use of a separate gRNA-encoding transcript for each site to be targeted. Separate gRNAs are not optimal for multiplex genome editing of cell populations as it is impossible to guarantee that each cell will express each gRNA; with multiple transcripts, cells get a complex and non-uniform random mixture of gRNAs. The present system, however, allows expression of multiple gRNAs from a single transcript, which allows targeting of multiple sites in the genome by expression of multiple gRNAs. Furthermore, with a single-transcript system, each cell should express all gRNAs with similar stoichiometry. This system could therefore easily be used to simultaneously alter expression of a large number of genes or to recruit multiple Cas9s or HFDs to a single gene, promoter, or enhancer. This capability will have broad utility, e.g., for basic biological research, where it can be used to study gene function and to manipulate the expression of multiple genes in a single pathway, and in synthetic biology, where it will enable researchers to create circuits in cell that are responsive to multiple input signals. The relative ease with which this technology can be implemented and adapted to multiplexing will make it a broadly useful technology with many wide-ranging applications.

The methods described herein include contacting cells with a nucleic acid encoding the multimeric gRNA cassettes described herein directed to one or more genes, and nucleic acids encoding Csy4 and Cas9, to thereby modulate expression of the one or more genes.

EXAMPLES

The invention is further described in the following examples, which do not limit the scope of the invention described in the claims.

Example 1. Multiplex Editing with CRISPR/Cas9

Figure 2:
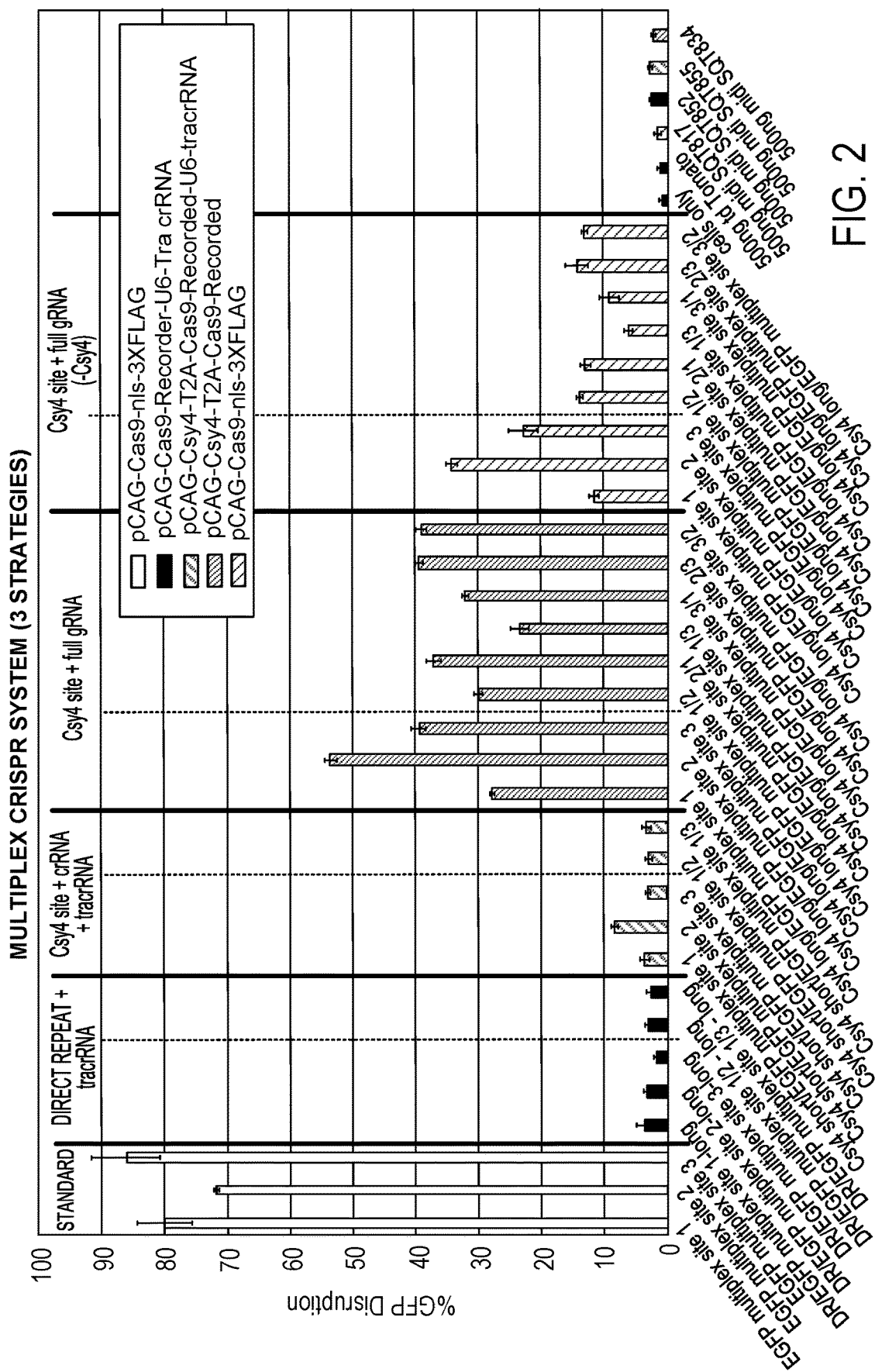
FIG. 2 is a bar graph showing the results of experiments in cells expressing the constructs shown in FIG. 1. The Csy4 site+full gRNA (constructs 5 and 6) was the most efficient multiplex framework.

Three strategies were tried with the objective of making multiplex edits with CRISPR/Cas9 from arrays of either crRNAs or sgRNAs expressed from a single transcript, as follows:
1. direct-repeat flanked crRNA array and Cas9, with separate tracrRNA
2. short crRNA array separated by Csy4 sites, expressed with Csy4, Cas9, and separate tracrRNA
3. full-length single guide RNAs (sgRNAs) separated by Csy4 sites Each set of constructs (illustrated in FIG. 1) was tested for the ability to efficiently disrupt EGFP in a U2OS-EGFP disruption assay. The results are shown in FIG. 2. Constructs designed using strategies 1 and 2 exhibited the lowest activity in the EGFP-disruption assay even for single targets; therefore further experiments (described below) focused on optimizing strategy 3.

Figure 3:
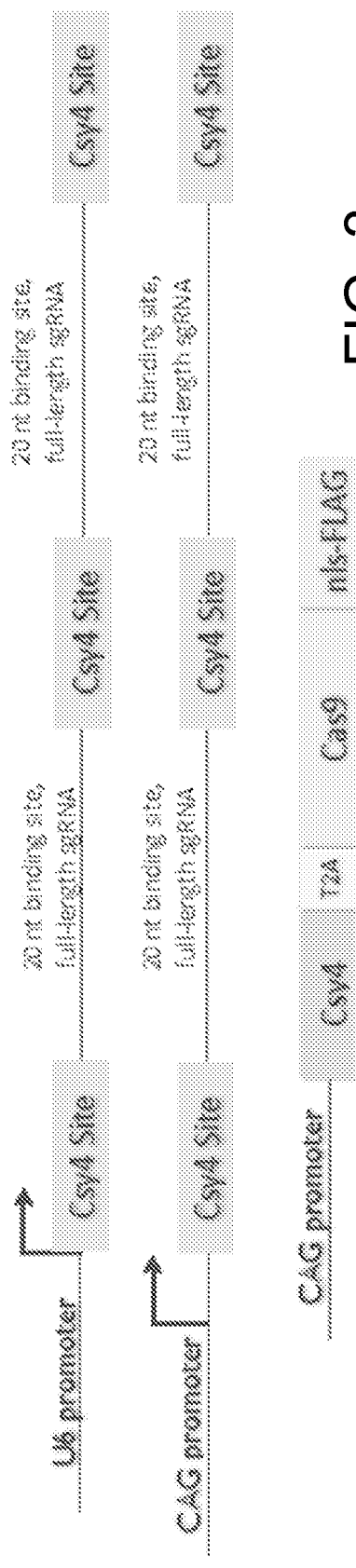
FIG. 3 is a schematic overview and comparison of exemplary standard and multiplex Csy4-based gRNA frameworks, and the transcripts they produce. Note that Csy4 enables the use of RNA Pol II promoters (e.g., CAG) as an alternative to U6, an RNA Pol III promoter.

Example 2. Multiplex Expression of Highly Active CRISPR Guide RNAs From RNA Polymerase II and III Promoters in Mammalian Cells A schematic overview of an exemplary strategy for cleaving gRNAs out from longer transcripts using the Csy4 nuclease is shown in FIG. 3. In initial experiments to demonstrate proof-of-concept, two versions of the Csy4-cleaved RNA hairpin site were tested for cleavage in human cells. To do this, gRNAs flanked by one of two Csy4 cleavage sites were expressed:

```
                                        (SEQ ID NO: 2)
1.   GTTCACTGCCGTATAGGCAGCTAAGAAA (full 28 nt)
                                        (SEQ ID NO: 1)
2.   GTTCACTGCCGTATAGGCAG (truncated 20 nt)
```

Figure 4:
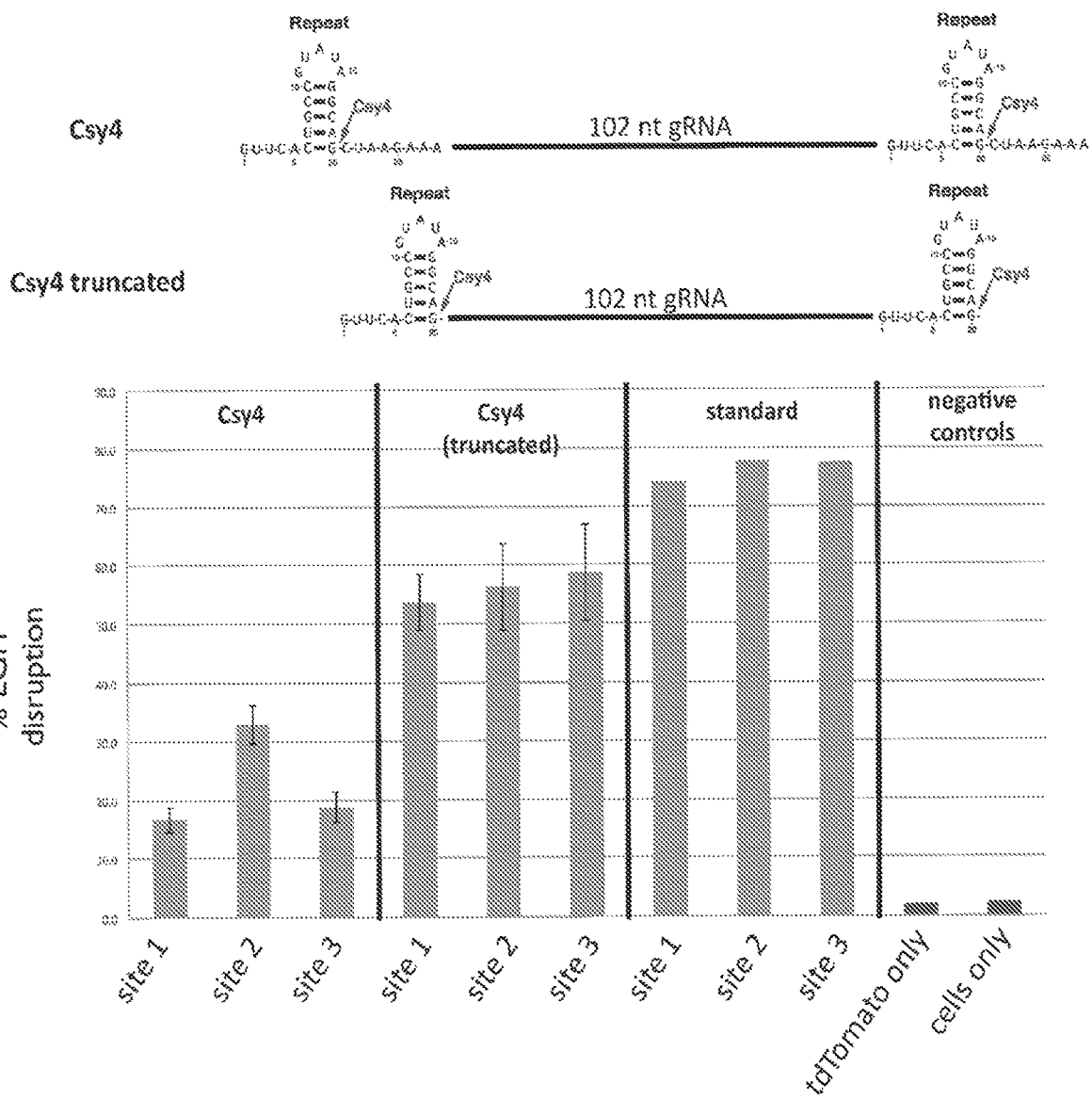
FIG. 4 is a bar graph showing that Csy4 cleaves a truncated recognition site producing gRNAs with higher activity in human cells. Processing of the truncated site also leaves a clean 5' end, effectively removing the 5' G restriction on gRNA target sequences imposed by the U6 promoter.

The results showed that gRNAs flanked on their 5' and 3' ends with the truncated 20 nt sequence were more active in mammalian cells than those flanked by the longer 28 nt sequence (FIG. 4). To the best of the present inventors' knowledge, this is the first demonstration that Csy4 nuclease can be used to process RNA transcripts in live human cells. One important additional advantage of the 20 nt truncated site is that, unlike the longer 28 nt sequence, it does not leave any additional nucleotides on the 5' end of a gRNA processed from the longer transcript (FIG. 4). This enables expression of gRNAs that have ANY desired nucleotide at the 5'-most position. This is an improvement relative to expression of gRNAs from RNA polymerase III promoters which have a requirement for specific nucleotide(s) at the 5'-most position.

Using this Csy4-based system, the efficient expression of two and three different gRNAs (FIGS. 5 and 6) was demonstrated. gRNAs simultaneously expressed using this approach induced alterations at the expected sites in human cells.

Figure 7:
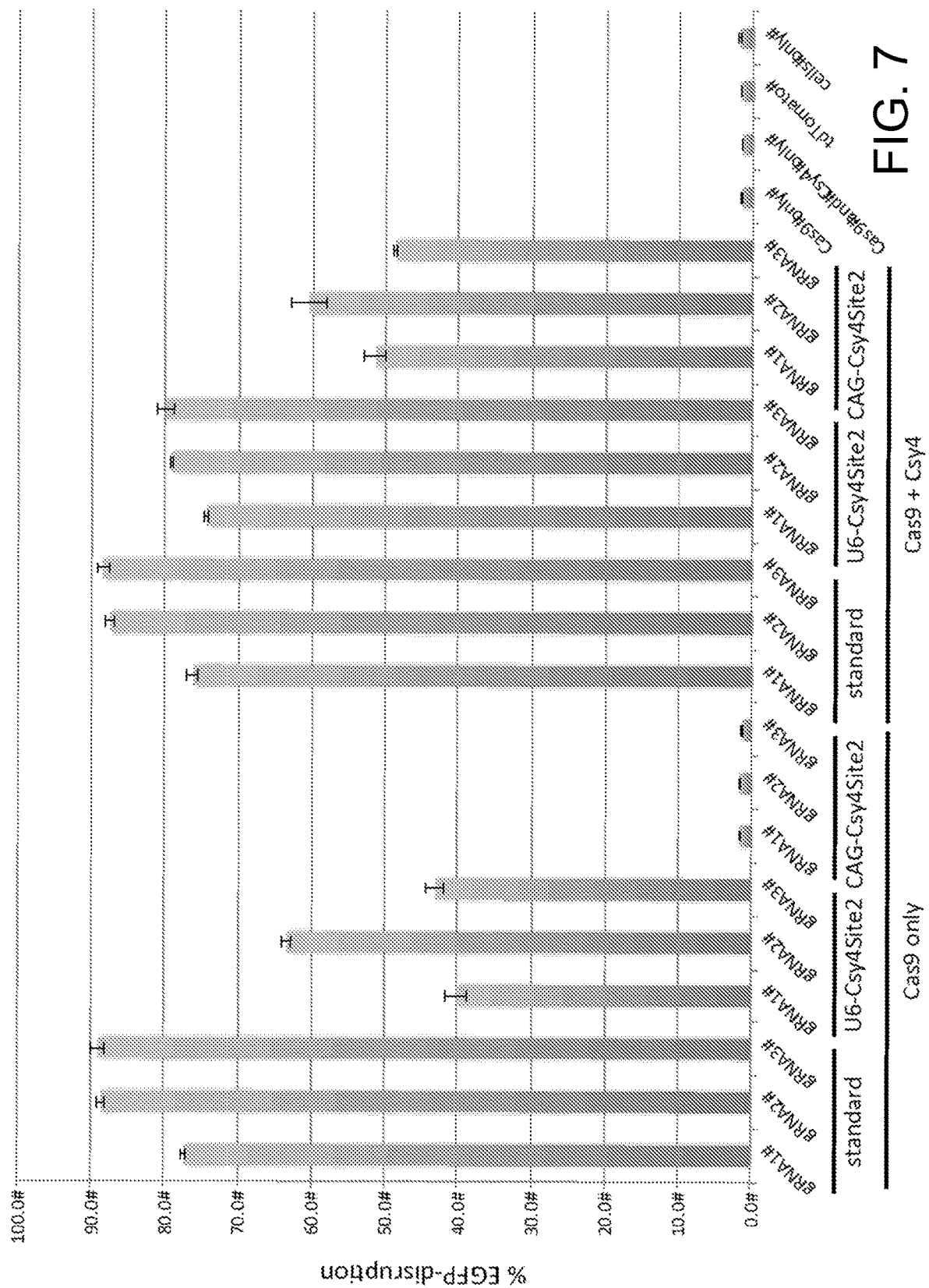
FIG. 7 is a bar graph showing gRNAs excised by Csy4 from RNA Pol II-transcribed mRNA can efficiently recruit Cas9 nuclease to specific targets in human cells. In these experiments, gRNAs were expressed in longer mRNA transcripts made from the RNA Pol II CAG promoter.

These results also demonstrated that this Csy4-based strategy could be used with gRNAs encoded on a longer mRNA produced by an RNA Pol II promoter (FIG. 7). In these experiments, one of three different single gRNAs flanked by the truncated Csy4 sites was encoded on an mRNA produced by the CAG promoter (an RNA Pol II promoter). As shown in FIG. 7, all three of these constructs could produce functional gRNA that could direct Cas9 nuclease in human cells but only in the presence of Csy4. The level of targeted Cas9 activity observed was comparable to (albeit somewhat lower than) what is observed when these gRNAs are expressed singly using a standard RNA Pol III promoter or as a Csy4-flanked transcript from an RNA Pol III promoter (FIG. 7).

In summary, the present results demonstrated that: 1) up to three functional gRNAs can be produced from a single RNA pol III transcript when separated by Csy4 cleavage sites and in the presence of Csy4 in human cells, 2) multiple Csy4-processed gRNAs can be used to direct Cas9 nuclease to introduce multiplex changes in a single human cell, and 3) a functional gRNA flanked by Csy4 cleavage sites can be excised by Csy4 nuclease from a longer mRNA transcript made from an RNA polymerase II promoter.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A deoxyribonucleic acid (DNA) molecule comprising: a plurality of sequences encoding guide RNAs (gRNAs), wherein each gRNA is flanked by at least one Csy4 cleavage sequence consisting of the sequence GTTCACTGCCGTATAGGCAG (SEQ ID NO:1), and the gRNA comprises the sequence:

($X_{17-20}$) GUUUUAGAGCUAUGCUGUUUUG; (SEQ ID NO: 4)

($X_{17-20}$) GUUUUAGAGCUA; (SEQ ID NO: 5)

($X_{17-20}$) GUUUUAGAGCUAUGCUGUUUUG; (SEQ ID NO: 6)

($X_{17-20}$) GUUUUAGAGCUAUGCU; (SEQ ID NO: 7)

($X_{17-20}$) GUUUUAGAGCUAGAAAUAGCAAGUUAAAAUAAGGCUAGUCCG; (SEQ ID NO: 8)

($X_{17-20}$) GUUUUAGAGCUAUGCUGAAAAGCAUAGCAAGUUAAAAUAAGGCUAGUCCGUUAUC; (SEQ ID NO: 9)

($X_{17-20}$) GUUUUAGAGCUAUGCUGUUUUGGAAACAAAACAGCAUAGCAAGUUAAAAUAAGGCUAGUCCGUUAUC; (SEQ ID NO: 10)

($X_{17-20}$) GUUUUAGAGCUAGAAAUAGCAAGUUAAAAUAAGGCUAGUCCGUUAUCAACUUGAAAAAGUGGCACCGAGUCGGUGC; (SEQ ID NO: 11)

-continued

```
                                           (SEQ ID NO: 12)
(X17-20) GUUUAAGAGCUAGAAAUAGCAAGUUUAAAUAAGGCUAGUCC

GUUAUCAACUUGAAAAAGUGGCACCGAGUCGGUGC;

(SEQ ID NO: 13)
(X17-20) GUUUUAGAGCUAUGCUGGAAACAGCAUAGCAAGUUUAAAUA

AGGCUAGUCCGUUAUCAACUUGAAAAAGUGGCACCGAGUCGGUGC;
or (SEQ ID NO: 14)
(X17-20) GUUUAAGAGCUAUGCUGGAAACAGCAUAGCAAGUUUAAAUA

AGGCUAGUCCGUUAUCAACUUGAAAAAGUGGCACCGAGUCGGUGC,
``` wherein $X_{17\text{-}20}$ is a sequence complementary to the complementary strand of 17-20 consecutive nucleotides of a target sequence.

2. The DNA molecule of claim 1, operably linked to a promoter sequence.

3. The DNA molecule of claim 2, wherein the promoter sequence is a RNA Polymerase II (Pol II) promoter or Pol III promoter.

4. The DNA molecule of claim 2, wherein the promoter sequence is a RNA Pol II promoter.

5. The DNA molecule of claim 4, wherein the Pol II promoter is selected from the group consisting of CAG, EF1A, CAGGS, PGK, UbiC, CMV, B29, Desmin, Endoglin, FLT-1, GFPA, and SYN1 promoters.

6. The DNA molecule of claim 1, comprising two, three, or more gRNA sequences.

7. The DNA molecule of claim 1, further comprising a sequence encoding a functional Csy4 enzyme.

8. The DNA molecule of claim 1, comprising one or more U at the 3' end of the molecule.

9. The DNA molecule of claim 1, wherein the target sequence is immediately 5' of a protospacer adjacent motif (PAM).

10. A DNA molecule comprising a promoter sequence linked with one, two, three or more cassettes, each cassette comprising: a sequence encoding a guide RNA (gRNA) linked to a Csy4 cleavage site consisting of the sequence GTTCACTGCCGTATAGGCAG (SEQ ID NO:1), and the gRNA comprises the sequence:

```
                                           (SEQ ID NO: 4)
(X17-20) GUUUUAGAGCUAUGCUGUUUUG;

(SEQ ID NO: 5)
(X17-20) GUUUUAGAGCUA;

(SEQ ID NO: 6)
(X17-20) GUUUUAGAGCUAUGCUGUUUUG;

(SEQ ID NO: 7)
(X17-20) GUUUUAGAGCUAUGCU;

(SEQ ID NO: 8)
(X17-20) GUUUUAGAGCUAGAAAUAGCAAGUUAAAAUAAGGCUAGUCC

G;

(SEQ ID NO: 9)
(X17-20) GUUUUAGAGCUAUGCUGAAAAGCAUAGCAAGUUAAAAUAAG

GCUAGUCCGUUAUC(XN);

(SEQ ID NO: 10)
(X17-20) GUUUUAGAGCUAUGCUGUUUUGGAAACAAAACAGCAUAGC

AAGUUAAAAUAAGGCUAGUCCGUUAUC;

(SEQ ID NO: 11)
(X17-20) GUUUUAGAGCUAGAAAUAGCAAGUUAAAAUAAGGCUAGUC

CGUUAUCAACUUGAAAAAGUGGCACCGAGUCGGUGC, (SEQ ID NO: 12)
(X17-20) GUUUAAGAGCUAGAAAUAGCAAGUUUAAAUAAGGCUAGUCC

GUUAUCAACUUGAAAAAGUGGCACCGAGUCGGUGC;

(SEQ ID NO: 13)
(X17-20) GUUUUAGAGCUAUGCUGGAAACAGCAUAGCAAGUUUAAAUA

AGGCUAGUCCGUUAUCAACUUGAAAAAGUGGCACCGAGUCGGUGC;
or (SEQ ID NO: 14)
(X17-20) GUUUAAGAGCUAUGCUGGAAACAGCAUAGCAAGUUUAAAUA

AGGCUAGUCCGUUAUCAACUUGAAAAAGUGGCACCGAGUCGGUGC,
``` wherein $X_{17\text{-}20}$ is a sequence complementary to the complementary strand of 17-20 consecutive nucleotides of a target sequence.

11. The DNA molecule of claim 10, comprising:
a Pol II promoter, operably linked to a first sequence encoding a first guide RNA linked to a Csy4 cleavage site, linked to a second sequence encoding a second guide RNA linked to a Csy4 cleavage site, linked to a third sequence encoding a third guide RNA linked to a Csy4 cleavage site.

12. The DNA molecule of claim 10, comprising a guide RNA sequence of about 100 nts.

13. The DNA molecule of claim 10, wherein the target sequence is immediately 5' of a protospacer adjacent motif (PAM).

14. An RNA molecule encoded by the DNA molecule of claim 1.

15. A method of producing a plurality of guide RNAs in a cell, the method comprising contacting the cell with the RNA molecule of claim 14.

16. The method of claim 15, wherein the cell is a mammalian cell and the cell also expresses an exogenous functional Csy4 enzyme sequence, or the method further comprises administering a functional Csy4 enzyme or nucleic acid encoding a functional Csy4 enzyme.

17. A vector comprising the DNA molecule of claim 1.

18. The vector of claim 17, further comprising a sequence encoding a functional Csy4 enzyme.

19. A method of producing a plurality of guide RNAs in a cell, the method comprising expressing the DNA molecule of claim 1 in the cell.

20. The method of claim 19, wherein the cell is a mammalian cell and the cell also expresses an exogenous functional Csy4 enzyme sequence, or the method further comprises administering a functional Csy4 enzyme or nucleic acid encoding a functional Csy4 enzyme.

\* \* \* \* \*

UNITED STATES PATENT AND TRADEMARK OFFICE
CERTIFICATE OF CORRECTION

PATENT NO.         : 10,526,589 B2
APPLICATION NO.    : 15/107550
DATED              : January 7, 2020
INVENTOR(S)        : Shengdar Tsai and J. Keith Joung Page 1 of 1

It is certified that error appears in the above-identified patent and that said Letters Patent is hereby corrected as shown below:

In the Claims

In Column 60, Line 5, Claim 10, delete "$C(X_N)$ ;" and insert -- C; --

In Column 60, Line 13 (approx.), Claim 10, delete "C," and insert -- C; --

Signed and Sealed this
Twentieth Day of October, 2020

Andrei Iancu
*Director of the United States Patent and Trademark Office*